United States Patent
Laaksonen

(10) Patent No.: US 11,474,116 B2
(45) Date of Patent: *Oct. 18, 2022

(54) CERAMIDES AND THEIR USE IN DIAGNOSING CVD

(71) Applicant: ZORA BIOSCIENCES OY, Espoo (FI)

(72) Inventor: Reijo Laaksonen, Lempaeaelae (FI)

(73) Assignee: ZORA BIOSCIENCES, OY, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 16/218,363

(22) Filed: Dec. 12, 2018

(65) Prior Publication Data

US 2019/0113531 A1    Apr. 18, 2019

Related U.S. Application Data

(63) Continuation of application No. 15/159,650, filed on May 19, 2016, now Pat. No. 10,197,582, which is a continuation of application No. 14/677,595, filed on Apr. 2, 2015, now Pat. No. 9,347,960.

(60) Provisional application No. 62/012,543, filed on Jun. 16, 2014.

(51) Int. Cl.
*G01N 33/92* (2006.01)
*A61K 31/164* (2006.01)
*C07B 59/00* (2006.01)

(52) U.S. Cl.
CPC .......... *G01N 33/92* (2013.01); *A61K 31/164* (2013.01); *C07B 59/001* (2013.01); *G01N 2405/08* (2013.01); *G01N 2458/15* (2013.01); *G01N 2800/32* (2013.01); *G01N 2800/324* (2013.01); *G01N 2800/50* (2013.01); *G01N 2800/52* (2013.01)

(58) Field of Classification Search
CPC .............. G01N 33/92; G01N 2405/08; G01N 2458/15; G01N 2800/324; G01N 2800/32; G01N 2800/50; G01N 2800/52; C07B 59/001; A61K 31/164
See application file for complete search history.

(56) References Cited

U.S. PATENT DOCUMENTS 9,347,960 B2 * 5/2016 Laaksonen ............ A61K 31/164
10,197,582 B2 * 2/2019 Laaksonen ............ C07B 59/001

FOREIGN PATENT DOCUMENTS

| WO | 2011/092285 A2 | 8/2011 | |
| WO | 2011138419 A1 | 11/2011 | |
| WO | 2011161062 A2 | 12/2011 | |
| WO | 2012/136856 A1 | 10/2012 | |
| WO | 2013/014286 A2 | 1/2013 | |
| WO | 2013068373 A2 | 5/2013 | |
| WO | 2013068374 A2 | 5/2013 | |
| WO | WO-2013068373 A2 * | 5/2013 | ............. G01N 33/92 |
| WO | 2014/060486 A1 | 4/2014 | |
| WO | 2014/135696 A1 | 9/2014 | |

OTHER PUBLICATIONS

Hsu et al., "Characterization of ceramides by low energy collisional-activated dissociation tandem mass spectrometry with negative-ion electrospray ionization", Journal of the American Society for Mass Spectrometry, May 1, 2002, vol. 13, No. 5, pp. 558-570.

Tikhonenko et al., "N-3 Polyunsaturated Fatty Acids Prevent Diabetic Retinopathy by Inhibition of Retinal Vascular Damage and Enhanced Endothelial Progenitor Cell Reparative Function", PLOS ONE, Jan. 29, 2013, vol. 8, No. 1, e55177, pp. 1-10.

Kujala et al., "Differential Network Analysis with Multiply Imputed Lipidomic Data", PLOS ONE, Mar. 30, 2015, vol. 10, No. 3, e0121449, pp. 1-18.

International Search Report and Written Opinion of the International Searching Authority dated Dec. 14, 2015 for International application No. PCT/EP2015/063492 (Authorized Officer, Titus Vogt), 19 pages.

Tarasov et al., "Molecular Lipids Identify Cardiovascular Risk and are Efficiently Lowered by Simvastatin and PCSK9 Deficiency", J Clin Endocrinol Metab, 99(1), Jan. 2014, pp. E45-E52.

\* cited by examiner

*Primary Examiner* — Shafiqul Haq
(74) *Attorney, Agent, or Firm* — MH2 Technology Law Group, LLP

(57) ABSTRACT

The present invention inter alia provides a method, and use thereof, of predicting CV complications such as AMI, ACS, stroke, and CV death by determining the concentrations of at least one ceramide of Group A and at least one ceramide of Group B in a biological sample and comparing those concentrations to a control. Finding a decreased concentration of at least one Group A ceramide and an increased concentration of at least one Group B ceramide indicates that the subject has an increased risk of developing one or more CV complications. Also provided are a newly identified subset of ceramide molecules, labelled versions thereof, and kits and compositions comprising the same for use in predicting and/or diagnosing CV complications.

11 Claims, 4 Drawing Sheets

Group A Ceramides

| Ceramide | OR per SD | OR 2nd Quartile | OR 3rd Quartile | OR 4th Quartile | AUC | Sens | Spec | MRC% | p-val | q-val |
|---|---|---|---|---|---|---|---|---|---|---|
| Cer(d18:2/25:0) | 0.57 (0.46-0.71) | 0.31 (0.17-0.54) | 0.21 (0.12-0.38) | 0.19 (0.11-0.35) | 0.66 (0.61, 0.71) | 0.59 | 0.66 | -20 | $3.5 \times 10^{-09}$ | $1.8 \times 10^{-09}$ |
| Cer(d16:1/24:0) | 0.65 (0.53-0.80) | 0.32 (0.18-0.57) | 0.22 (0.12-0.39) | 0.21 (0.12-0.38) | 0.66 (0.60, 0.71) | 0.56 | 0.72 | -18 | $4.8 \times 10^{-09}$ | $2.4 \times 10^{-09}$ |
| Cer(d18:2/24:0) | 0.61 (0.50-0.76) | 0.22 (0.12-0.40) | 0.19 (0.10-0.34) | 0.20 (0.11-0.37) | 0.66 (0.61, 0.71) | 0.51 | 0.79 | -17 | $5.9 \times 10^{-09}$ | $2.9 \times 10^{-09}$ |
| Cer(d18:2/26:0) | 0.60 (0.48-0.74) | 0.47 (0.27-0.82) | 0.28 (0.16-0.49) | 0.28 (0.16-0.49) | 0.65 (0.60, 0.70) | 0.6 | 0.65 | -19 | $2.5 \times 10^{-08}$ | $1.2 \times 10^{-08}$ |
| Cer(d18:1/26:0) | 0.65 (0.53-0.80) | 0.28 (0.16-0.50) | 0.30 (0.17-0.54) | 0.25 (0.14-0.44) | 0.63 (0.58, 0.69) | 0.51 | 0.72 | -14 | $1.0 \times 10^{-06}$ | $4.0 \times 10^{-07}$ |
| Cer(d18:1/26:0) | 0.69 (0.56-0.85) | 0.35 (0.20-0.60) | 0.35 (0.20-0.60) | 0.25 (0.14-0.45) | 0.64 (0.58, 0.69) | 0.56 | 0.69 | -15 | $2.2 \times 10^{-06}$ | $8.2 \times 10^{-07}$ |
| Cer(d18:1/25:0) | 0.65 (0.53-0.80) | 0.55 (0.32-0.96) | 0.37 (0.21-0.64) | 0.29 (0.17-0.51) | 0.63 (0.57, 0.68) | 0.57 | 0.64 | -13 | $3.4 \times 10^{-06}$ | $1.2 \times 10^{-06}$ |
| Cer(d18:1/23:0) | 0.76 (0.63-0.93) | 0.42 (0.24-0.73) | 0.36 (0.21-0.63) | 0.33 (0.19-0.57) | 0.62 (0.57, 0.67) | 0.55 | 0.65 | -13 | $9.6 \times 10^{-06}$ | $3.2 \times 10^{-06}$ |
| Cer(d16:1/25:0) | 0.74 (0.61-0.90) | 0.36 (0.20-0.63) | 0.25 (0.14-0.45) | 0.33 (0.19-0.58) | 0.61 (0.56, 0.67) | 0.56 | 0.65 | -12 | $2.4 \times 10^{-05}$ | $7.7 \times 10^{-06}$ |
| Cer(d18:2/23:0) | 0.82 (0.67-0.99) | 0.31 (0.17-0.54) | 0.23 (0.13-0.41) | 0.36 (0.20-0.62) | 0.61 (0.56, 0.67) | 0.49 | 0.79 | -9 | $1.6 \times 10^{-04}$ | $4.6 \times 10^{-05}$ |

FIG. 1

| Group B Ceramides | | | | | | | | | |
|---|---|---|---|---|---|---|---|---|---|
| Ceramide | OR per SD | OR 2nd Quartile | OR 3rd Quartile | OR 4th Quartile | AUC | Sens | Spec | MRC% | p-val | q-val |
| Cer(d18:1/22:1) | 2.21 (1.68-2.90) | 1.40 (0.80-2.44) | 2.64 (1.52-4.59) | 5.50 (3.07-9.84) | 0.69 (0.64, 0.74) | 0.57 | 0.76 | 31 | $2.8*10^{-11}$ | $2.1*10^{-11}$ |
| Cer(d18:1/24:2) | 2.17 (1.68-2.80) | 1.10 (0.63-1.91) | 2.08 (1.21-3.59) | 4.67 (2.63-8.29) | 0.67 (0.62, 0.72) | 0.58 | 0.71 | 26 | $3.5*10^{-10}$ | $2.1*10^{-10}$ |
| Cer(d18:1/18:0) | 2.18 (1.70-2.79) | 1.14 (0.66-1.99) | 2.25 (1.30-3.89) | 4.86 (2.73-8.65) | 0.67 (0.62, 0.72) | 0.6 | 0.69 | 32 | $4.9*10^{-10}$ | $2.9*10^{-10}$ |
| Cer(d18:1/16:0) | 1.99 (1.58-2.52) | 0.98 (0.56-1.69) | 2.00 (1.16-3.43) | 3.94 (2.24-6.94) | 0.66 (0.61, 0.71) | 0.67 | 0.59 | 20 | $2.7*10^{-09}$ | $1.5*10^{-09}$ |
| Cer(d18:0/18:0) | 1.91 (1.48-2.45) | 1.19 (0.68-2.07) | 2.42 (1.40-4.19) | 4.25 (2.41-7.50) | 0.65 (0.60, 0.70) | 0.63 | 0.63 | 42 | $5.9*10^{-08}$ | $2.6*10^{-08}$ |
| Cer(d18:1/23:1) | 1.79 (1.43-2.23) | 0.87 (0.50-1.50) | 1.59 (0.93-2.72) | 3.51 (2.00-6.16) | 0.65 (0.60, 0.70) | 0.65 | 0.6 | 21 | $7.9*10^{-08}$ | $3.4*10^{-08}$ |
| Cer(d18:1/24:1) | 1.69 (1.36-2.12) | 1.38 (0.80-2.38) | 1.66 (0.97-2.86) | 3.92 (2.23-6.90) | 0.64 (0.58, 0.69) | 0.52 | 0.72 | 24 | $2.0*10^{-06}$ | $7.5*10^{-07}$ |
| Cer(d18:0/16:0) | 1.59 (1.28-1.96) | 1.28 (0.74-2.20) | 1.72 (1.00-2.96) | 3.46 (1.98-6.05) | 0.62 (0.57, 0.68) | 0.64 | 0.58 | 14 | $1.0*10^{-05}$ | $3.5*10^{-06}$ |
| Cer(d18:1/26:2) | 1.51 (1.23-1.86) | 1.18 (0.69-2.02) | 1.32 (0.77-2.26) | 2.62 (1.51-4.54) | 0.60 (0.55, 0.66) | 0.6 | 0.57 | 17 | $2.7*10^{-04}$ | $7.3*10^{-05}$ |
| Cer(d16:1/16:0) | 1.32 (1.09-1.60) | 0.84 (0.49-1.44) | 1.10 (0.64-1.87) | 1.79 (1.04-3.07) | 0.57 (0.52, 0.62) | 0.5 | 0.65 | 10 | $2.1*10^{-02}$ | $4.3*10^{-03}$ |

FIG. 2

| Ceramides Not Failing Within Groups A or B | | | | | | | | | |
|---|---|---|---|---|---|---|---|---|---|
| Ceramide | OR per SD | OR 2nd Quartile | OR 3rd Quartile | OR 4th Quartile | AUC | Sens | Spec | MRC% | p-val | q-val |
| Cer(d16:1/20:0) | 1.02 (0.85-1.24) | 0.52 (0.30-0.89) | 0.65 (0.38-1.12) | 0.61 (0.35-1.04) | 0.47 (0.42, 0.53) | 0.45 | 0.56 | 1 | 0.44 | 0.069 |
| Cer(d18:2/20:0) | 1.00 (0.83-1.21) | 0.79 (0.46-1.34) | 0.56 (0.33-0.96) | 0.85 (0.50-1.04) | 0.47 (0.42, 0.53) | 0.44 | 0.53 | 0 | 0.48 | 0.073 |
| Cer(d18:2/26:1) | 0.89 (0.74-1.08) | 0.95 (0.56-1.62) | 0.63 (0.37-1.08) | 0.73 (0.43-1.25) | 0.54 (0.49, 0.59) | 0.57 | 0.53 | -5 | 0.21 | 0.035 |
| Cer(d18:2/21:0) | 0.92 (0.76-1.11) | 0.61 (0.35-1.04) | 0.82 (0.48-1.39) | 0.56 (0.33-0.96) | 0.55 (0.49, 0.60) | 0.46 | 0.64 | -4 | 0.25 | 0.041 |
| Cer(d18:1/16:1) | 0.94 (0.78-1.14) | 0.54 (0.32-0.93) | 0.82 (0.48-1.39) | 0.85 (0.50-1.45) | 0.51 (0.45, 0.56) | 0.53 | 0.47 | -2 | 0.43 | 0.068 |
| Cer(d16:1/21:0) | 0.99 (0.82-1.20) | 0.88 (0.52-1.50) | 0.85 (0.50-1.44) | 0.91 (0.54-1.55) | 0.52 (0.47, 0.57) | 0.47 | 0.65 | 0 | 0.54 | 0.082 |

FIG. 3

CERAMIDES AND THEIR USE IN DIAGNOSING CVD

CROSS REFERENCE TO RELATED APPLICATIONS

This application is a continuation of U.S. application Ser. No. 15/159,650 filed 19 May 2016 (Allowed), which is a continuation of U.S. application Ser. No. 14/677,595 filed 2 Apr. 2015 (U.S. Pat. No. 9,347,960), which claims priority to and the benefit of U.S. Provisional Application No. 62/012,543 filed on 16 Jun. 2014, the entire contents of which are incorporated herein by reference.

FIELD

This application relates generally to ceramide biomarkers and their use in identifying subjects having an increased risk for developing cardiovascular (CV) complications, such as AMI (acute myocardial infarction), ACS (acute coronary syndrome), stroke or CV death.

BACKGROUND

Current CV markers, LDL-C, HDL-C, and total cholesterol, are not able to identify coronary artery disease (CAD) patients or subjects that have an elevated risk for CV complications, such as AMI, ACS, stroke and CV death, from patients having more stable disease.

The term myocardial infarction pathologically denotes the death of cardiac myocytes due to extended ischemia, which may be caused by an increase in perfusion demand or a decrease in blood flow. The event is called "acute" if it is sudden and serious. Diagnosis of AMI is determined by a high clinical suspicion from history and physical examination, in addition to changes in cardiac biomarkers (creatinine kinase MB [CK-MB], troponins, and myoglobin) and electrocardiogram (ECG) findings. Imaging techniques, such as two-dimensional echocardiography, are also useful in demonstrating myocardial dysfunction. Current CV markers, LDL-C, HDL-C, and total cholesterol, however, only identify when the damage of heart tissue has already occurred. They fail to predict the likelihood of the CVD complication occurring.

Acute coronary syndrome (ACS) is a term used for any condition brought on by sudden, reduced blood flow to the heart. The first sign of acute coronary syndrome can be sudden stopping of the heart called cardiac arrest. Acute coronary syndrome is often diagnosed in an emergency room or hospital with same cardiac biomarkers or electrocardiogram (ECG) as AMI, that provide evidence on damaged heart tissue or problems in heart's electric activity.

A stroke is the loss of brain function due to a disturbance in the blood supply to the brain, depriving brain tissue of oxygen and food. Within minutes, brain cells begin to die. A stroke may be caused by a blocked artery (ischemic stroke) or a leaking or burst blood vessel (hemorrhagic stroke). Some people may experience a temporary disruption of blood flow through their brain (transient ischemic attack, or TIA). Strokes are usually diagnosed by brain imaging and carrying out physical tests.

Sudden cardiac death (SCD) is a sudden, unexpected death caused by loss of heart function, also named as sudden cardiac arrest (SCA). Sudden cardiac arrest is not a heart attack (myocardial infarction). Heart attacks occur when there is a blockage in one or more of the coronary arteries, preventing the heart from receiving enough oxygen-rich blood. In contrast, sudden cardiac arrest occurs when the electrical system to the heart malfunctions and suddenly becomes very irregular. The heart beats dangerously fast. Ventricular fibrillation may occur, and blood is not delivered to the body. In the first few minutes, the greatest concern is that blood flow to the brain will be reduced so drastically that a person will lose consciousness. Death follows unless emergency treatment is begun immediately. Sudden cardiac arrest happens without warning and is rarely diagnosed with medical tests as its happening. Instead, SCA often is diagnosed after it happens, by ruling out other causes of a person's sudden collapse.

AMI, ACS, stroke and sudden cardiac death are diagnosed in acute stage, but predictive markers are not available. The risk factors behind these events are for example, age, hypolipidemia, hypertension, smoking, diabetes, CAD or previous heart attack. Yet, no diagnostic test that could predict the events exists, and cardiovascular diseases are the leading cause of death worldwide. Furthermore, CVD costs for society more than any other group of diseases. The same tests that are used for diagnosing CVD are utilized in predicting the events. Today the most innovative approach is to use LDL-C, HDL-C, Lp(a), Lp-PLA2 (PLAC test) or CRP. However, none of the listed lipid based markers (LDL-C, HDL-C, Lp(a), Lp-PLA2 (PLAC test)) provide clinically useful predictive information allowing stratification aid to physicians. CRP has been promising in the research setting, however it has proven to be unspecific (CRP is an acute phase reactant that can react to many different stimuli leading to highly variable test results) and thus CRP values are difficult to interpret in the clinical use. There is an unmet need for a diagnostic test that could predict CV complications, such as AMI (acute myocardial infarction), ACS (acute coronary syndrome), stroke and CV death.

The ceramide based risk stratification offers superior p-values compared to any other lipid based biomarker today. Furthermore, the levels of plasma ceramides can be affected with specific lipid lowering treatments (such as statins) and, therefore, ceramide markers offer precise and actionable risk stratification.

A large group of lipid molecules, including certain ceramides, and ratios calculated from two lipid molecules have been identified for predicting CV outcomes in CAD patients who are undergoing statin treatment or who are not undergoing statin treatment (Zora Biosciences patent applications WO2013068373 and WO2013068374) or for identifying high-risk CAD patients or predicting whether a subject is at risk for developing CV complications (Zora Biosciences patent application U.S. Ser. No. 13/695,766 and U.S. Ser. No. 13/805,319).

However, there remains a need for improved methods of predicting the risk of a patient developing a CV complication, such as AMI, ACS, stroke, and CV death.

SUMMARY

This application discloses a unique rule for selecting combinations of ceramides based on their structure and using them to predict CVD/CAD-associated complications, including AMI, ACS, stroke, and CV death. These ceramide markers thus provide a means to identify and treat high-risk coronary artery disease patients. These sensitive and specific ceramide markers were specifically tested to display superior diagnostic and prognostic value compared to the current clinically-used markers predictive for CVD/CAD outcomes. Using combinations of ceramide biomarkers according to the newly established rule will facilitate earlier intervention, less symptom development and suffering and decreased morbidity/mortality associated with CVD. Thus, the combination of ceramide markers described and claimed herein allow for individual tailoring of treatment, drug intervention and follow-up for patients being at risk to develop major CV complications, such as AMI, ACS, stroke, and CV death.

According to this newly identified rule, certain ceramides have been classified into separate groups based on their structure and their association, when combined, (based on either an increased or decreased concentration) with an increased risk to develop CV complications, such as AMI, ACS, stroke, and CV death. Thus, in certain embodiments, the methods involve determining the concentration of at least one ceramide of Formula (I) (Group A ceramide) and at least one ceramide of Formula (II) (Group B ceramide) in a biological sample obtained from a subject.

A decreased concentration of at least one ceramide of Formula (I), when combined with an increased concentration of at least one ceramide of Formula (II) associates with an increased risk of a subject developing a CVD complication, such as AMI, ACS, stroke, and CV death.

Ceramides of Formula (I) have the following structure:

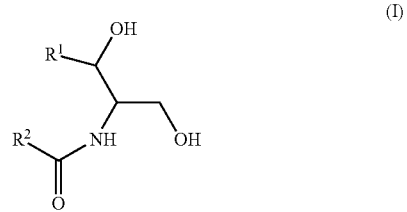

(I)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms.

Ceramides of Formula (II) have the following structure:

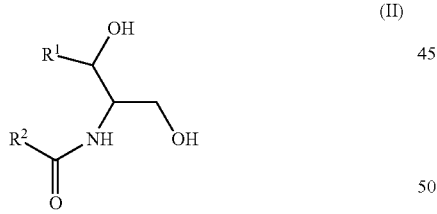

(II)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms.

In one embodiment, the method of determining whether a subject is at risk to develop one or more CV complications comprises the steps of: a) determining the concentration of at least one Group A ceramide in a biological sample obtained from the subject, b) determining the concentration of at least one Group B ceramide in the biological sample obtained from the subject, c) comparing the concentration of the at least one ceramide of Group A and the concentration of the at least one ceramide of Group B to a control sample; and d) determining that the subject has an increased risk of developing one or more CV complications, if the sample contains a decreased concentration of the at least one ceramide of Group A and an increased concentration of the at least one ceramide of Group B, as compared to the control sample. In certain embodiments, the method further comprises a step of spiking the biological sample with at least one deuterium-labelled ceramide of Formula I and at least one deuterium-labelled ceramide of Formula II prior to determining the concentration of the at least one ceramide of Formula I and II.

In one embodiment, the concentrations of the following ceramides of Formula (II) are determined: Cer(d18:1/16:0), Cer(d18:1/18:0), and Cer(d18:1/24:1). In another embodiment, the concentration of the following ceramide of Formula (I): Cer(d18:1/24:0) and the concentrations of the following ceramides of Formula (II): Cer(d18:1/16:0), Cer (d18:1/18:0), and Cer(d18:1/24:1) are determined.

Another aspect is directed to a subset of Group A ceramides and/or a subset of Formula B ceramides that were previously not known to exist in human blood samples and their use in methods of determining whether a subject is at risk to develop one or more CV complications, such as AMI, ACS, stroke, and CV death. Thus, in certain embodiments, the methods involve determining the concentration of at least one ceramide of Formula (III) (Group C ceramide) and at least one ceramide of Formula (IV) (Group D ceramide) in a biological sample obtained from a subject.

A decreased concentration of at least one ceramide of Formula (III), when combined with an increased concentration of at least one ceramide of Formula (IV) associates with an increased risk of a subject developing a CV complication, such as AMI, ACS, stroke, and CV death.

Ceramides of Formula (III) have the following structure:

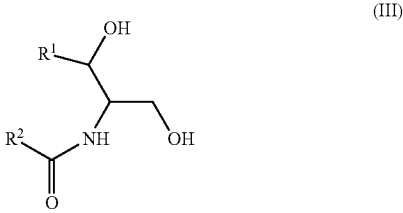

(III)

wherein $R^1$ is a mono-unsaturated alkyl chain having 13 carbon atoms or a di-unsaturated alkyl chain having 15 carbon atoms, and wherein $R^2$ is a saturated alkyl chain having 21-23 or 25 carbon atoms.

Ceramides of Formula (IV) have the following structure:

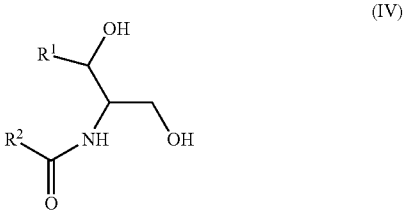

(IV)

wherein $R^1$ is a mono-unsaturated alkyl chain having 13 carbon atoms and $R^2$ is a saturated alkyl chain having 15 or 17 carbon atoms, a mono-unsaturated alkyl chain having 23 carbon atoms, or a di-unsaturated alkyl chain having 23 carbon atoms; or wherein $R^1$ is a di-unsaturated alkyl chain having 15 carbon atoms and $R^2$ is a saturated alkyl chain having 15 or 17 carbon atoms, a mono-unsaturated alkyl chain having 21-23 carbon atoms, or a di-unsaturated alkyl chain having 23 carbon atoms.

In one embodiment, the method of determining whether a subject is at risk to develop one or more CV complications comprises the steps of: a) determining the concentration of at least one Group C ceramide in a biological sample obtained from the subject, b) determining the concentration of at least one Group D ceramide in the biological sample obtained from the subject, c) comparing the concentration of the at least one ceramide of Group C and the concentration of the at least one ceramide of Group D to a control sample; and d) determining that the subject has an increased risk of developing one or more CV complications, if the sample contains a decreased concentration of the at least one ceramide of Group C and an increased concentration of the at least one ceramide of Group D, as compared to the control sample. In certain embodiments, the method further comprises a step of spiking the biological sample with at least one deuterium-labelled ceramide of Formula III and at least one deuterium-labelled ceramide of Formula IV prior to determining the concentration of the at least one ceramide of Formula III and IV.

In certain embodiments, the concentrations of the at least one ceramide of Formula (I) and the at least one ceramide of Formula (II) or the at least one ceramide of Formula (III) and the at least one ceramide of Formula (IV) are determined according to the following equations: Z=(ceramide of Formula I)$^a$/(ceramide of Formula II)$^b$ or Z=(ceramide of Formula III)$^a$/(ceramide of Formula IV)$^b$, wherein a, b$\in$R.

Another aspect relates to a method for evaluating the effectiveness of a treatment of CVD and/or one or more of its complications, such as AMI, ACS, stroke, and CV death, in a subject, the method comprising the steps of a) determining the concentration of at least one Group A ceramide (or at least one Group C ceramide) in a biological sample obtained from the subject, b) determining the concentration of at least one Group B ceramide (or at least one Group D ceramide) in the biological sample obtained from the subject, c) comparing the concentration of the at least one ceramide of Group A (or at least one Group C ceramide) and the concentration of the at least one ceramide of Group B (or at least one Group D ceramide) to a control sample; and d) determining that the treatment is effective if the sample contains an equal or increased concentration of the at least one ceramide of Group A (or at least one Group C ceramide) and an equal or decreased concentration of the at least one ceramide of Group B (or at least one Group D ceramide), as compared to the control sample.

In certain embodiments, the method for evaluating the effectiveness of a treatment of atherosclerosis or CVD and/or one or more of its complications in the subject may further comprise after the determining step, changing, supplementing, or keeping the same an already administered treatment in the subject based on the concentrations of the at least one ceramide of Group A and the at least one ceramide of Group B obtained in the determining step.

Yet another aspect relates to a method of choosing an appropriate treatment of CVD and/or one or more of its complications, such as AMI, ACS, stroke, and CV death, in a subject, the method comprising the steps of a) determining the concentration of at least one Group A ceramide (or at least one Group C ceramide) in a biological sample obtained from the subject, b) determining the concentration of at least one Group B ceramide (or at least one Group D ceramide) in the biological sample obtained from the subject, c) comparing the concentration of the at least one ceramide of Group A (or at least one Group C ceramide) and the concentration of the at least one ceramide of Group B (or at least one Group D ceramide) to a control sample; and d) determining that the subject is in need of treatment or a change in, or supplementation of, an already administered treatment if the sample contains a decreased concentration of the at least one ceramide of Group A (or at least one Group C ceramide) and an increased concentration of the at least one ceramide of Group B (or at least one Group D ceramide), as compared to the control sample.

In one embodiment, the treatment, the effectiveness of which is to be evaluated or which is to be chosen as appropriate in accordance with the methods described and claimed herein, is a lipid modifying treatment (e.g., statin or other lipid lowering drug as described elsewhere in this application). In another embodiment, the method further comprises a step of administering to the subject the treatment that the subject is determined to be in need of in step (d).

Yet another aspect relates to a method of treating or preventing CVD and/or one or more of its complications, such as AMI, ACS, stroke, and CV death, in a subject, the method comprising administering to the subject a therapeutically effective dose of a drug, wherein the drug is a statin; another lipid lowering drug selected from an HMG-CoA reductase inhibitor other than a statin, niacin (nicotinic acid), a cholesterol absorption inhibitor, a cholesteryl ester transfer protein (CETP), a bile acid sequestrant, a fibrate, a phytosterol, and a PCSK9 inhibitor; or a modulator of lipid/lipid concentration ratios selected from a small molecule, an antibody, an antisense RNA, a small interfering RNA (siRNA), and a natural or modified lipid, and wherein before administering the drug the subject has been identified as suffering from or having an increased risk of developing a CVD complication, such as AMI, ACS, stroke, and CV death based on a decreased concentration of at least ceramide of Group A (or at least one ceramide of Group C) and an increased concentration of at least one ceramide of Group B (or at least one ceramide of Group D) as compared to a control sample.

The concentrations of ceramides in the biological samples can be determined using any currently available technique or later developed technology. In certain embodiments, the concentrations of the ceramides are determined using mass spectrometry. In certain embodiments, the mass spectrometry instrument is coupled to a direct sample infusion method or to a high performance separation method.

The biological sample from the subject and the control sample is preferably a blood sample, more preferably a blood plasma sample, or also preferably a blood serum sample. In certain embodiments, the blood sample is a blood spot dried on a filter. It may also be a fraction of blood, blood plasma or blood serum, e.g., a lipid fraction thereof. Thus, in certain embodiments, the methods comprise a further step of extracting the lipids from the biological sample before determining the concentrations of the Group A, B, C and/or D ceramides. Alternatively, both the sample from the subject and the control sample may be a tissue sample, e.g., artery tissue, such as carotid artery tissue, or artery plaque material, such as carotid artery plaque material.

Yet another aspect is a composition or kit for predicting CV complications or for performing any of the methods disclosed herein. In certain embodiments, the composition or kit comprises at least one isotope (e.g., deuterium)- labelled ceramide of Formula I and/or at least one ceramide of Formula (II). In one embodiment, the kit comprises the following isotope (e.g., deuterium)-labelled ceramides of Formula (II): Cer(d18:1/16:0), Cer(d18:1/18:0), and Cer (d18:1/24:1). In another embodiment, the kit comprises the following isotope (e.g., deuterium)-labelled ceramide of Formula (I): Cer(d18:1/24:0) and the following isotope (e.g., deuterium)-labelled ceramides of Formula (II): Cer(d18:1/16:0), Cer(d18:1/18:0), and Cer(d18:1/24:1).

Another embodiment is directed to a composition or kit comprising at least one isotope (e.g., deuterium)-labelled ceramide of Formula (III) and/or at least one isotope (e.g., deuterium)-labelled ceramide of Formula (IV).

BRIEF DESCRIPTION OF THE DRAWINGS

The accompanying drawings, which are incorporated in and constitute a part of this specification, illustrate certain embodiments, and together with the written description, serve to explain certain principles of the compositions and methods disclosed herein.

FIG. 1 shows the mean relative changes/differences (the difference of case versus control group means divided by the mean concentration of the control group) of ten Group A ceramide species with the lowest Student's t-test p-values.

FIG. 2 shows the mean relative changes/differences (the difference of case versus control group means divided by the mean concentration of the control group) of ten Group B ceramide species with the lowest Student's t-test p-values.

FIG. 3 shows the mean relative changes/differences (the difference of case versus control group means divided by the mean concentration of the control group) of six ceramide species that do not fall within either of the Group A or Group B ceramides.

DETAILED DESCRIPTION

Figure 4:
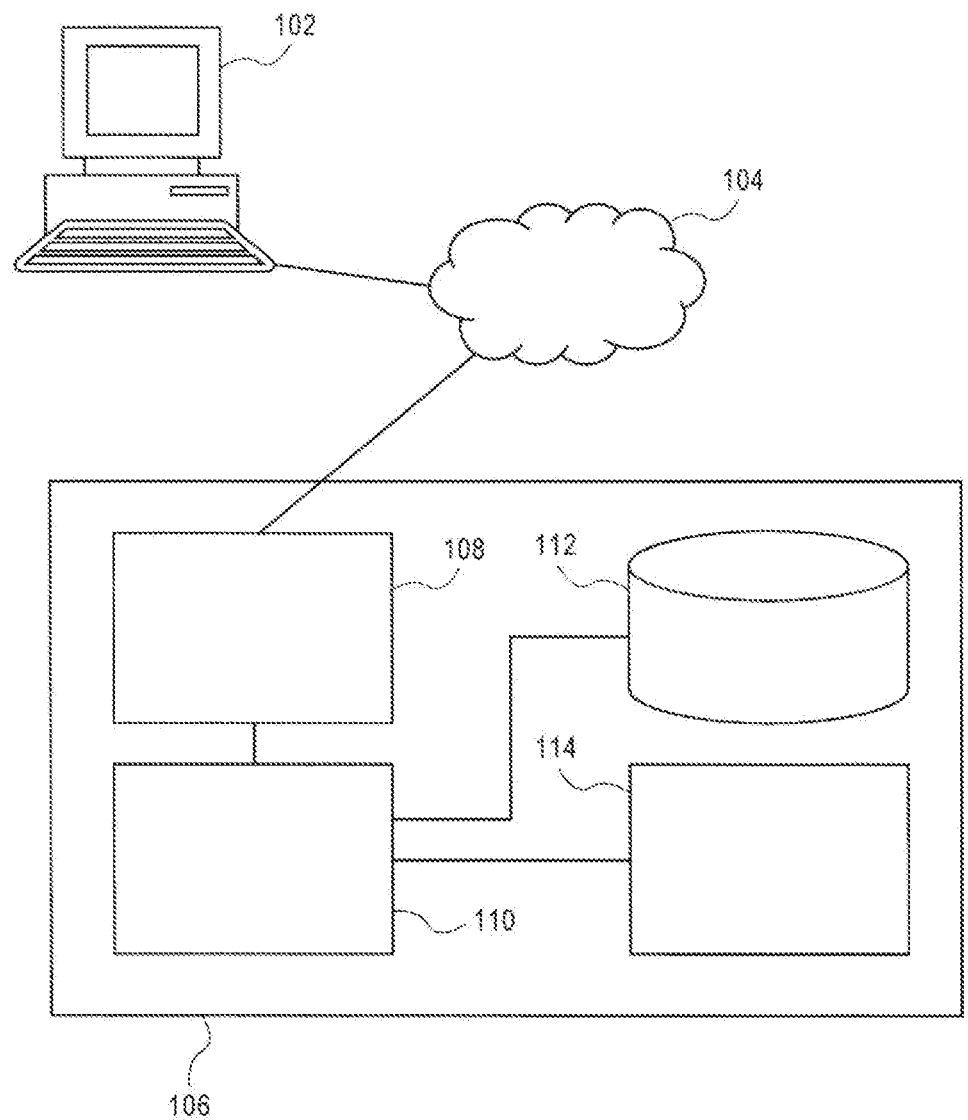
FIG. 4 provides a schematic diagram of a system according to some embodiments of the invention. In particular, this figure illustrates various hardware, software, and other resources that may be used in implementations of computer system 106 according to disclosed systems and methods.

Reference will now be made in detail to various exemplary embodiments, examples of which are illustrated in the accompanying drawings and discussed in the detailed description that follows. It is to be understood that the following detailed description is provided to give the reader a fuller understanding of certain embodiments, features, and details of aspects of the invention, and should not be interpreted as limiting the scope of the invention.

1. Abbreviations

Unless indicated otherwise, the abbreviations used in this application have the following meanings: LDL-C: low density lipoprotein cholesterol; HDL-C: high density lipoprotein cholesterol; CVD: cardiovascular disease; CV: cardiovascular; CAD: coronary artery disease; IVUS: intravascular ultrasound; NIRS: near infrared spectroscopy; OCT: Optical coherence tomography; CABG: Coronary artery bypass surgery; MS: mass spectrometry; OR: odds ratio; SD: standard deviation; AUC: area under curve; Sens: sensitivity; Spec: specificity; MRC %: Mean relative change; p-val: P-value; q-val: and Q-value; Pr(>Chi): Chi-square; ICD-10: International Statistical Classification of Diseases and Related Health Problems 10th Revision.

2. Definitions

In order that the present invention may be more readily understood, certain terms are first defined. Additional definitions are set forth throughout the detailed description.

The terms "subject," "host," "patient," and "individual" are used interchangeably herein to refer to any mammalian subject for whom diagnosis or therapy is desired, particularly humans. The subject may have previously suffered from a cardiovascular disease event such as angina pectoris, myocardial infarction or stroke. The CVD may or may not be a result of atherosclerosis. Or the subject may be a healthy individual with no previous signs of CVD.

Coronary vascular disease/cardiovascular disease (CVD) has its general meaning in the art and is used to classify numerous conditions that affect the heart, heart valves, blood, and vasculature of the body, including CAD. In the present disclosure the terms CVD and CAD may be used interchangeably. Cardiovascular diseases include endothelial dysfunction, coronary artery disease, angina pectoris, myocardial infarction, atherosclerosis, congestive heart failure, hypertension, cerebrovascular disease, stroke, transient ischemic attacks, deep vein thrombosis, peripheral artery disease, cardiomyopathy, arrhythmias, aortic stenosis, and aneurysm. Such diseases frequently involve atherosclerosis. In a preferred embodiment of the invention, the cardiovascular disease is a cardiovascular disease associated with atherosclerosis.

As used herein, the term "computer-implemented method" means a method which utilizes a machine or apparatus to achieve its objective.

As used herein, the term "processor" means a device which is capable of interpreting and executing instructions. Specifically, a processor employs logic circuitry to receive input data and provide the appropriate output data. Processors can communicate with each other via a network.

As used in this application, a "Group A ceramide," "ceramide of Group A," or the like means a ceramide of Formula (I):

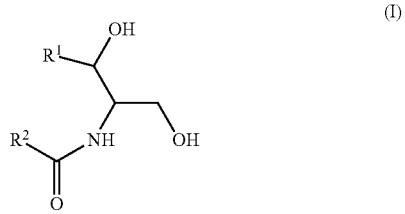

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms.

As used in this application, a "Group B ceramide," "ceramide of Group B," or the like means a ceramide of Formula (II):

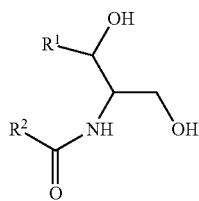

(II)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms.

As used in this application, a "Group C ceramide," "ceramide of Group C," or the like means a ceramide of Formula (III):

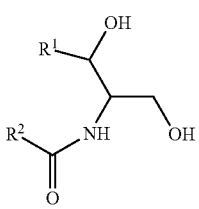

(III)

wherein $R^1$ is a mono-unsaturated alkyl chain having 13 carbon atoms or a di-unsaturated alkyl chain having 15 carbon atoms, and wherein $R^2$ is a saturated alkyl chain having 21-23 or 25 carbon atoms.

As used in this application, a "Group D ceramide," "ceramide of Group D," or the like means a ceramide of Formula (IV):

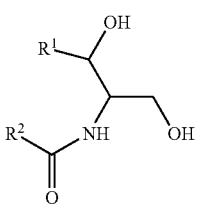

(IV)

wherein $R^1$ is a mono-unsaturated alkyl chain having 13 carbon atoms and $R^2$ is a saturated alkyl chain having 15 or 17 carbon atoms, a mono-unsaturated alkyl chain having 23 carbon atoms, or a di-unsaturated alkyl chain having 23 carbon atoms; or wherein $R^1$ is a di-unsaturated alkyl chain having 15 carbon atoms and $R^2$ is a saturated alkyl chain having 15 or 17 carbon atoms, a mono-unsaturated alkyl chain having 21-23 carbon atoms, or a di-unsaturated alkyl chain having 23 carbon atoms.

As used herein, a "lipid lowering drug" according to the invention is preferably an HMG-CoA reductase inhibitor, niacin (nicotinic acid), a cholesterol absorption inhibitor, a cholesteryl ester transfer protein (CETP) inhibitor, a bile acid sequestrant, a fibrate, a phytosterol or a PCSK9 inhibitor.

As used herein, a "cholesterol absorption inhibitor" is preferably ezetimibe or SCH-48461; a cholesteryl ester transfer protein (CETP) inhibitor is preferably evacetrapib, anacetrapib or dalcetrapib; a bile acid sequestrant is preferably colesevelam, cholestyramine or colestipol; a fibrate is preferably fenofibrate, gemfibrozil, clofibrate, or bezafibrate, and the PCSK9 inhibitor is selected from a PCSK9 specific antibody, an siRNA, and a peptidomimetic.

3. Ceramide Structure and Nomenclature

Ceramide molecules consists of sphingoid base (SB) and a fatty acid (FA) chain. The structure of one representative ceramide molecule is shown below.

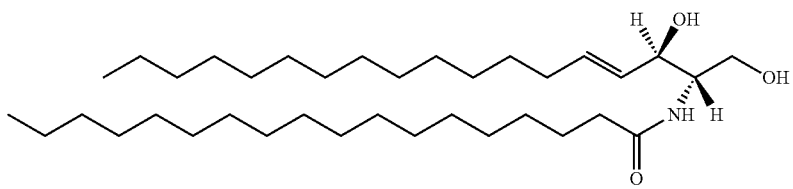 [SMILES: CCCCCCCCCCCCC/C=C/[C@@H](O)[C@H](CO)NC(=O)CCCCCCCCCCCCCCCCC]

This Cer(d18:1/18:0) lipid is a Group B ceramide, where $R^1$ is a mono-unsaturated alkyl chain having 15 carbon atoms and $R^2$ is a saturated alkyl chain having 17 carbon atoms.

The nomenclature of ceramides is typically presented as a first pair of numbers corresponding to the SB and a second pair of numbers corresponding to the FA. For example, in the Cer(d18:1/18:0) molecule above, the first number pair (d18:1) refers to the SB and the second number pair (18:0) refers to the FA. In SB and FA nomenclature, the first number of each pair refers to the number of carbon atoms in the SB or FA chain, while the second number refers to the number of carbon-carbon double bonds of the SB or FA chain. Thus, in Cer(d18:1/18:0), the SB has 18 carbon atoms and one carbon-carbon double bond, while the FA has 18 carbon atoms and no carbon-carbon double bonds. FAs can be saturated or unsaturated depending on whether they have double bonds in their structure. For example, the FA 16:1 is an unsaturated FA with 16 carbon atoms and one carbon-carbon double bond, while the FA 18:0 is a saturated FA with 18 carbon atoms and no carbon-carbon double bonds.

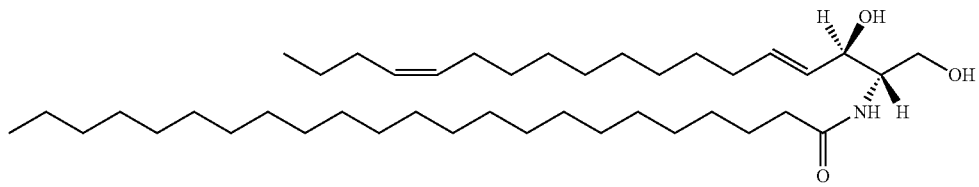 [SMILES: CCC/C=C\CCCCCCCC/C=C/[C@@H](O)[C@H](CO)NC(=O)CCCCCCCCCCCCCCCCCCCCCC]

By way of further example, the structure of Cer(d18:2/23:0) is as follows:
This lipid is a Group A ceramide, where $R^1$ is a di-unsaturated alkyl chain having 15 carbon atoms and $R^2$ is a saturated alkyl chain having 22 carbon atoms.

By way of further example, the structure of Cer(d16:1/22:1) is as follows:

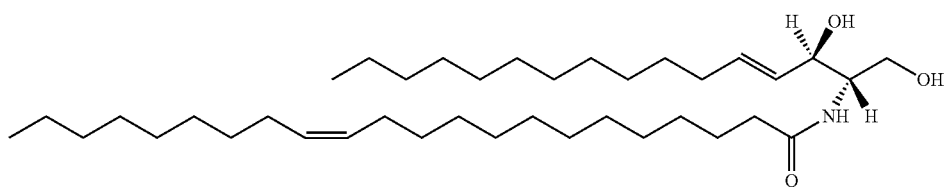 [SMILES: CCCCCCCC/C=C\CCCCCCCCCCCC(=O)N[C@@H](CO)[C@H](O)/C=C/CCCCCCCCCCC]

This lipid is a Group B ceramide, where $R^1$ is a mono-unsaturated alkyl chain having 13 carbon atoms and $R^2$ is a mono-unsaturated alkyl chain having 21 carbon atoms.

In the de novo ceramide synthesis, the first double bond to the SB is formed in carbon 4, forming SBs d16:1 and d18:1. The second double bond of the SB is most commonly located in carbon 14, forming SB d18:2.

The double bond in the FA chain may be in various positions depending on the length of the FA chain and the number of carbon-carbon double bonds. In the 22:1 FA, the most common double bond position is in carbon 13. In the 23:1 FA, the most common double bond position is in carbon 14. In the 24:1 FA, the most common double bond position is in position 15. In the 24:2 and 26:2 FAs, the most common double bond positions are in carbons 5 and 9.

4. Diagnostic Methods

Disclosed herein are methods for predicting CV complications including AMI, ACS, stroke and cardiovascular death, by measuring certain combinations of ceramides in a biological sample. Ceramides have been implicated in the pathogenesis of CVD based on animal experiments, while the data in humans is largely lacking. We have recently shown the association of certain lipids, including certain distinct ceramide molecules, with CV mortality (U.S. Ser. No. 13/695,766, U.S. Ser. No. 13/805,319, WO2013068373, WO2013068374 and Tarasov et al. 2014).

For diagnostic use, a marker should have as high sensitivity and specificity as possible. Sensitivity measures the proportion of cases that are correctly classified as a case by the marker, and specificity measures the proportion of controls that are correctly classified as a control by the marker. For diagnostic use it is important that high enough percentage of subjects that are going to have a CV event in the future will be identified for targeted treatments at early stages. However, for limiting the treatment costs, markers with high specificity are preferred over markers with low specificity.

For example, a test with sensitivity of 0.7 would imply that among a population of 100 000 patients, that are going to face a CV event, 70 000 would be identified as having high risk for the event by the test. With a specificity of 0.2, among a population of 100 000 patients with stable CVD but with no forthcoming severe events, only 20 000 would be correctly identified of being low risk, while 80 000 would be falsely identified of being at high risk. This would mean that the targeted treatment cost for 80 000 patients would be used in vain. In contrast, if an alternative test with a specificity value of 0.8 for the same event had been used, only 20 000 patients would be falsely identified having high risk for severe event. Compared to the low specificity test, this would save the treatment costs for 60 000 patients.

This application discloses a rule for selecting a combination of ceramides to identify patients having increased risk for developing CV complications with significantly improved sensitivity and specificity. This improved sensitivity and specificity is determined by the structure of the ceramides that fall within two distinct classes, such that a decreased concentration of at least one ceramide from the first structural class and an increased concentration of at least one ceramide from the second structural class, indicate an increased risk for developing CV complications. Specific combinations of ceramide species from both classes, selected according to the disclosed rule, are superior in predicting CV complications compared to traditional risk markers or individual ceramide molecules or a ratio thereof.

The improved diagnostic cannot be achieved by randomly selecting a combination of ceramide species. Instead, the ceramide combinations should be selected according to the rule disclosed herein by combining at least one ceramide with a very long saturated fatty acid and at least one ceramide with either long chain saturated fatty acid or very long chain unsaturated fatty acid. Specifically selected combinations of ceramides showed improved diagnostic sensitivity and specificity as compared to individual ceramides or ratios derived from two lipid molecules. The disease associated specificity of these specific combinations of ceramides is determined by the structure of the ceramide species and the biological function of various ceramide synthases that make the members of the ceramide class.

Concentrations of ceramides with very long saturated fatty acid chains (from 22:0 to 26:0) are lower in persons having an increased risk for CV complications (Group A ceramide). On the other hand, concentrations of ceramides with long chain saturated fatty acids (16:0 and 18:0) and very long chain unsaturated fatty acid (from 22:1 to 26:2) are higher in persons having an increased risk of CV complications (Group B ceramides). The diagnosis of CV complications improves when at least one Group A ceramide and at least one Group B ceramide are measured, instead of selecting, for example, two Group A or Group B ceramides.

The two distinct classes of ceramides that were found to provide improved diagnostic power when combined are shown in the table below, where the ceramide species for Group A include one of the listed sphingoid bases (SB) and one of the listed fatty acids (FA), and where the ceramide species for Group B include one of the listed sphingoid bases (SB) and one of the listed fatty acids (FA).

| Group A (decreasing concentration) Ceramides with very long saturated FA | | |
|---|---|---|
| SB | | FA |
| d16:1 | + | 22:0 |
| d18:0 | | 23:0 |
| d18:1 | | 24:0 |
| d18:2 | | 25:0 |
| | | 26:0 |

| Group B (increasing concentration) Ceramides with long chain saturated FA and very long chain unsaturated FA | | |
|---|---|---|
| SB | | FA |
| d16:1 | + | 16:0 |
| d18:0 | | 18:0 |
| d18:1 | | 22:1 |
| d18:2 | | 23:1 |
| | | 24:1 |
| | | 24:2 |
| | | 26:2 |

It is also possible to define the two structural classes of ceramides by chemical formulae. The Group A ceramides (decreasing concentration associated with an increased risk of CV complications) have a structure according to Formula I:

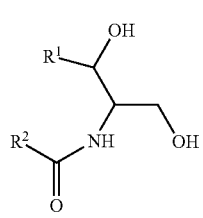

(I)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms.

The Group B ceramides (increasing concentration associated with an increased risk of CV complications) have a structure according to Formula II:

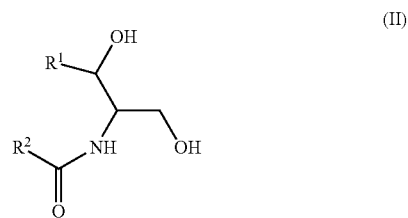

(II)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms.

The Group A and Group B ceramides can also be classified by the function of the ceramide synthases that are responsible for their synthesis. Six different ceramide synthases (CerS1-6) have been characterized in humans. Based on known specificity of ceramide synthases (CerS) for FA substrates, Group B ceramides contain ceramides exclusively produced by CerS1, S4, S5 and S6, that are known to synthesize ceramides with long FAs (14-18 carbons). Fatty acids with very-long FA (≥22 carbon atoms), synthesized by CerS2 and S3, are found in both Groups A and B. However, the very-long ceramide molecules in Group A are saturated, while the very-long ceramides in Group B are unsaturated. Thus, the products of CerS2 and S3 are placed into Groups A or B depending on the saturation level.

By categorizing certain ceramides into distinct groups based on structure and/or the specificity of the ceramide synthases for fatty acid substrates found within the ceramides, this application discloses a rule for selecting a combination of ceramides with significantly improved sensitivity and specificity for identifying patients having increased risk for developing CV complications.

In a particular embodiment, a method is provided for determining whether a subject is at risk to develop one or more CV complications, such as AMI, ACS, stroke, and CV death, wherein the method comprises (a) determining in a biological sample obtained from the subject the concentration of at least one ceramide of Formula I:

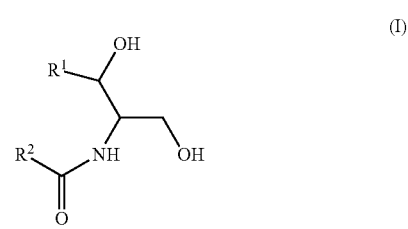

(I)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms;

(b) determining in the biological sample from the subject the concentration of at least one ceramide of Formula II:

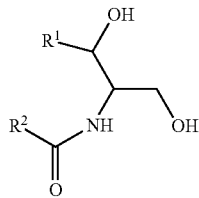

(II)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms;

(c) comparing the concentration of the at least one ceramide of Formula I and the concentration of the at least one ceramide of Formula II to a control sample; and (d) determining that the subject has an increased risk of developing one or more CV complications, if the biological sample contains a decreased concentration of the at least one ceramide of Formula I and an increased concentration of the at least one ceramide of Formula II, as compared to the control sample.

Another aspect relates to a method for evaluating the effectiveness of a treatment of CVD and/or one or more of its complications, such as AMI, ACS, stroke, and CV death, in a subject, the method comprising the steps of (a) determining in a biological sample obtained from the subject the concentration of at least one ceramide of Formula I:

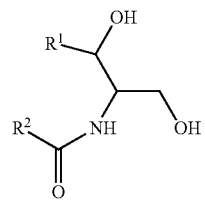

(I)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms;

(b) determining in the biological sample from the subject the concentration of at least one ceramide of Formula II:

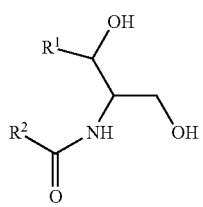

(II)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms;

(c) comparing the concentration of the at least one ceramide of Formula I and the concentration of the at least one ceramide of Formula II to a control sample; and (d) determining that the treatment is effective if the sample contains an equal or increased concentration of the at least one ceramide of Formula I and an equal or decreased concentration of the at least one ceramide of Formula II, as compared to the control sample.

Yet another aspect relates to a method of choosing an appropriate treatment of CVD and/or one or more of its complications, such as AMI, ACS, stroke, and CV death, in a subject, the method comprising:

(a) determining in a biological sample obtained from the subject the concentration of at least one ceramide of Formula I:

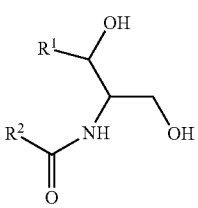

(I)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms;

(b) determining in the biological sample from the subject the concentration of at least one ceramide of Formula II:

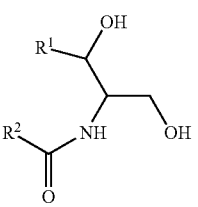

(II)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms;

(c) comparing the concentration of the at least one ceramide of Formula I and the concentration of the at least one ceramide of Formula II to a control sample; and (d) determining that the subject is in need of treatment or a change in, or supplementation of, an already administered treatment if the sample contains a decreased concentration of the at least one ceramide of Formula I and an increased concentration of the at least one ceramide of Formula II, as compared to the control sample.

In one embodiment of the aforementioned methods, the concentrations of at least 2, at least 3, at least 4, at least 5, or at least 6 ceramides of Formula I are determined. In another embodiment, the concentrations of at least 2, at least 3, at least 4, at least 5, or at least 6 ceramides of Formula II are determined. In yet another embodiment, the concentrations of at least 2, at least 3, at least 4, at least 5, or at least 6 ceramides of Formula I are determined and the concentrations of at least 2, at least 3, at least 4, at least 5, or at least 6 ceramides of Formula II are determined.

In one embodiment of the aforementioned methods, the concentrations of at least one of the following ceramides of Formula (II) are determined: Cer(d18:1/16:0), Cer(d18:1/18:0), and Cer(d18:1/24:1). In certain embodiments, the following Formula (II) ceramides or combinations thereof may be determined in the aforementioned methods:

| Formula (II) | Formula (II) | Formula (II) |
|---|---|---|
| Cer(d18:1/16:0) | | |
| Cer(d18:1/18:0) | | |
| Cer(d18:1/24:1) | | |
| Cer(d18:1/16:0) | Cer(d18:1/18:0) | |
| Cer(d18:1/16:0) | Cer(d18:1/24:1) | |
| Cer(d18:1/18:0) | Cer(d18:1/24:1) | |
| Cer(d18:1/16:0) | Cer(d18:1/18:0) | Cer(d18:1/24:1) |

In another embodiment, the concentration of the following ceramide of Formula (I): Cer(d18:1/24:0) and the concentrations of at least one of the following ceramides of Formula (II): Cer(d18:1/16:0), Cer(d18:1/18:0), and Cer(d18:1/24:1) are determined. In certain embodiments, the concentrations of the following combinations of Formula (I) and Formula (II) ceramides may be determined in the aforementioned methods:

| Formula (I) | Formula (II) | Formula (II) | Formula (II) |
|---|---|---|---|
| Cer(d18:1/24:0) | Cer(d18:1/16:0) | | |
| Cer(d18:1/24:0) | Cer(d18:1/18:0) | | |
| Cer(d18:1/24:0) | Cer(d18:1/24:1) | | |
| Cer(d18:1/24:0) | Cer(d18:1/16:0) | Cer(d18:1/18:0) | |
| Cer(d18:1/24:0) | Cer(d18:1/16:0) | Cer(d18:1/24:1) | |
| Cer(d18:1/24:0) | Cer(d18:1/18:0) | Cer(d18:1/24:1) | |
| Cer(d18:1/24:0) | Cer(d18:1/16:0) | Cer(d18:1/18:0) | Cer(d18:1/24:1) |

Another aspect is directed to a subset of Group A ceramides and a subset of Group B ceramides that were previously not known to exist in human blood samples and their use in methods of determining whether a subject is at risk to develop one or more CV complications, such as AMI, ACS, stroke, and CV death. The newly identified ceramides are listed in Table 1 below:

TABLE 1

| Newly Identified d16:1 and d18:2 Ceramides | |
|---|---|
| d16:1 ceramides | d18:2 ceramides |
| Cer(d16:1/16:0) | Cer(d18:2/16:0) |
| Cer(d16:1/18:0) | Cer(d18:2/18:0) |
| Cer(d16:1/22:0) | Cer(d18:2/22:0) |
| Cer(d16:1/23:0) | Cer(d18:2/22:1) |
| Cer(d16:1/24:0) | Cer(d18:2/23:0) |
| Cer(d16:1/24:1) | Cer(d18:2/23:1) |

TABLE 1-continued

| Newly Identified d16:1 and d18:2 Ceramides | |
|---|---|
| d16:1 ceramides | d18:2 ceramides |
| Cer(d16:1/24:2) | Cer(d18:2/24:0) |
| Cer(d16:1/26:0) | Cer(d18:2/24:1) |
| | Cer(d18:2/24:2) |
| | Cer(d18:2/26:0) |

The newly identified ceramides that represent a subset of the Group A ceramides have the structure of Formula III:

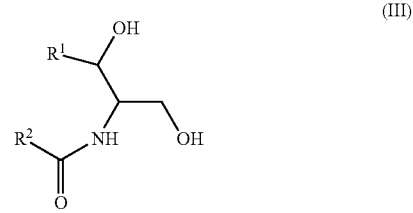

(III)

wherein $R^1$ is a mono-unsaturated alkyl chain having 13 carbon atoms or a di-unsaturated alkyl chain having 15 carbon atoms, and wherein $R^2$ is a saturated alkyl chain having 21-23 or 25 carbon atoms.

The newly identified ceramides that represent a subset of the Group B ceramides have the structure of Formula IV:

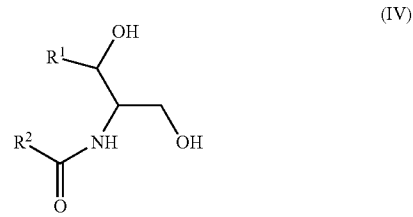

(IV)

wherein $R^1$ is a mono-unsaturated alkyl chain having 13 carbon atoms and $R^2$ is a saturated alkyl chain having 15 or 17 carbon atoms, a mono-unsaturated alkyl chain having 23 carbon atoms, or a di-unsaturated alkyl chain having 23 carbon atoms; or wherein $R^1$ is a di-unsaturated alkyl chain having 15 carbon atoms and $R^2$ is a saturated alkyl chain having 15 or 17 carbon atoms, a mono-unsaturated alkyl chain having 21-23 carbon atoms, or a di-unsaturated alkyl chain having 23 carbon atoms.

Accordingly, certain embodiments are directed to a method for determining whether a subject is at risk to develop one or more CV complications, such as AMI, ACS, stroke, and CV death, wherein the method comprises (a) determining in a biological sample obtained from the subject the concentration of at least one ceramide of Formula III:

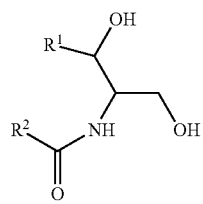

(III)

wherein $R^1$ is a mono-unsaturated alkyl chain having 13 carbon atoms or a di-unsaturated alkyl chain having 15 carbon atoms, and wherein $R^2$ is a saturated alkyl chain having 21-23 or 25 carbon atoms;

(b) determining in the biological sample from the subject the concentration of at least one ceramide of Formula IV:

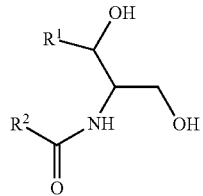

(IV)

wherein $R^1$ is a mono-unsaturated alkyl chain having 13 carbon atoms and $R^2$ is a saturated alkyl chain having 15 or 17 carbon atoms, a mono-unsaturated alkyl chain having 23 carbon atoms, or a di-unsaturated alkyl chain having 23 carbon atoms; or wherein $R^1$ is a di-unsaturated alkyl chain having 15 carbon atoms and $R^2$ is a saturated alkyl chain having 15 or 17 carbon atoms, a mono-unsaturated alkyl chain having 21-23 carbon atoms, or a di-unsaturated alkyl chain having 23 carbon atoms;

(c) comparing the concentration of the at least one ceramide of Formula III and the concentration of the at least one ceramide of Formula IV to a control sample; and (d) determining that the subject has an increased risk of developing one or more CV complications, if the biological sample contains a decreased concentration of the at least one ceramide of Formula III and an increased concentration of the at least one ceramide of Formula IV, as compared to the control sample.

Another aspect relates to a method for evaluating the effectiveness of a treatment of CVD and/or one or more of its complications, such as AMI, ACS, stroke, and CV death, in a subject, the method comprising:

(a) determining in a biological sample obtained from the subject the concentration of at least one ceramide of Formula III:

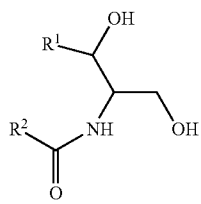

(III)

wherein $R^1$ is a mono-unsaturated alkyl chain having 13 carbon atoms or a di-unsaturated alkyl chain having 15 carbon atoms, and wherein $R^2$ is a saturated alkyl chain having 21-23 or 25 carbon atoms;

(b) determining in the biological sample from the subject the concentration of at least one ceramide of Formula IV:

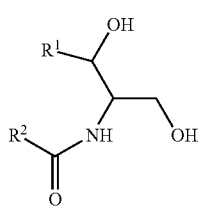

(IV)

wherein $R^1$ is a mono-unsaturated alkyl chain having 13 carbon atoms and $R^2$ is a saturated alkyl chain having 15 or 17 carbon atoms, a mono-unsaturated alkyl chain having 23 carbon atoms, or a di-unsaturated alkyl chain having 23 carbon atoms; or wherein $R^1$ is a di-unsaturated alkyl chain having 15 carbon atoms and $R^2$ is a saturated alkyl chain having 15 or 17 carbon atoms, a mono-unsaturated alkyl chain having 21-23 carbon atoms, or a di-unsaturated alkyl chain having 23 carbon atoms;

(c) comparing the concentration of the at least one ceramide of Formula III and the concentration of the at least one ceramide of Formula IV to a control sample; and (d) determining that the treatment is effective if the sample contains an equal or increased concentration of the at least one ceramide of Formula III and an equal or decreased concentration of the at least one ceramide of Formula IV, as compared to the control sample.

Yet another aspect relates to a method of choosing an appropriate treatment of CVD and/or one or more of its complications, such as AMI, ACS, stroke, and CV death, in a subject, the method comprising the steps of (a) determining in a biological sample obtained from the subject the concentration of at least one ceramide of Formula III:

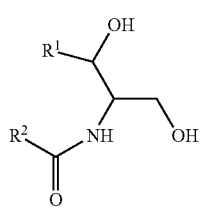

(III)

wherein $R^1$ is a mono-unsaturated alkyl chain having 13 carbon atoms or a di-unsaturated alkyl chain having 15 carbon atoms, and wherein $R^2$ is a saturated alkyl chain having 21-23 or 25 carbon atoms;

(b) determining in the biological sample from the subject the concentration of at least one ceramide of Formula IV:

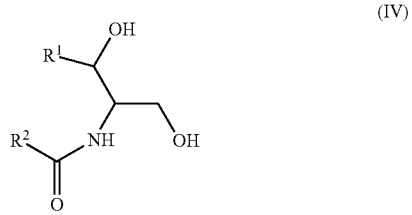

wherein $R^1$ is a mono-unsaturated alkyl chain having 13 carbon atoms and $R^2$ is a saturated alkyl chain having 15 or 17 carbon atoms, a mono-unsaturated alkyl chain having 23 carbon atoms, or a di-unsaturated alkyl chain having 23 carbon atoms; or wherein $R^1$ is a di-unsaturated alkyl chain having 15 carbon atoms and $R^2$ is a saturated alkyl chain having 15 or 17 carbon atoms, a mono-unsaturated alkyl chain having 21-23 carbon atoms, or a di-unsaturated alkyl chain having 23 carbon atoms;

(c) comparing the concentration of the at least one ceramide of Formula III and the concentration of the at least one ceramide of Formula IV to a control sample; and (d) determining that the subject is in need of treatment or a change in, or supplementation of, an already administered treatment if the sample contains a decreased concentration of the at least one ceramide of Formula III and an increased concentration of the at least one ceramide of Formula IV, as compared to the control sample.

In one embodiment of the aforementioned methods, the concentrations of at least 2, at least 3, at least 4, at least 5, or at least 6 ceramides of Formula III are determined. In another embodiment, the concentrations of at least 2, at least 3, at least 4, at least 5, or at least 6 ceramides of Formula IV are determined. In yet another embodiment, the concentrations of at least 2, at least 3, at least 4, at least 5, or at least 6 ceramides of Formula III are determined and the concentrations of at least 2, at least 3, at least 4, at least 5, or at least 6 ceramides of Formula IV are determined.

In certain embodiments of the aforementioned methods, the concentrations of the at least one ceramide of Formula (I) and the at least one ceramide of Formula (II) or the at least one ceramide of Formula (III) and the at least one ceramide of Formula (IV) are determined according to the following equations: $Z=(\text{ceramide of Formula I})^a/(\text{ceramide of Formula II})^b$ or $Z=(\text{ceramide of Formula III})^a/(\text{ceramide of Formula IV})^b$, wherein a, b$\in$R and (ceramide of Formula I), (ceramide of Formula II), (ceramide of Formula III), and (ceramide of Formula IV) refer to the concentration of the ceramide of Formula I, the concentration of the ceramide of Formula II, the concentration of the ceramide of Formula III, and the concentration of the ceramide of Formula IV, respectively. According to this embodiment the subject has an increased risk of developing one or more CV complications, if the biological sample contains an increased Z value, as compared to the control sample. In other embodiment the equation is used for determining that the treatment is effective if the sample contains an equal or decreased Z value, as compared to the control sample. In another embodiment the Z value is calculated for determining that the subject is in need of treatment or in need of adjusting the level of the treatment according to the appropriate guidelines on treating cardiovascular patients and the prescribed regimens and dosing therein if the sample contains an increased Z value, as compared to the control sample.

It may be useful and even advantageous for the methods and uses described herein to further comprise a step of determining the serum level of total cholesterol, low-density lipoprotein cholesterol (LDL-C), high-density lipoprotein cholesterol (HDL-C), Apolipoprotein A-I, Apolipoprotein A-II, and/or Apolipoprotein B (ApoB) and/or Apolipoprotein C-III (ApoC-III) in a sample from said subject. Furthermore, according to one embodiment of the disclosed methods or uses, the subject is preferably one that does not have elevated serum levels of one or more of total cholesterol, low-density lipoprotein cholesterol (LDL-C), Apolipoprotein C-III (ApoC-III) or Apolipoprotein B (ApoB), or a decreased serum level of HDL-cholesterol (HDL-C).

5. Detection Methods

Also disclosed herein are methods of detecting in a biological sample obtained from a subject the concentration of at least one ceramide of Formula I and at least one ceramide of Formula II, wherein the method comprises:

(a) determining in a biological sample obtained from the subject the concentration of at least one ceramide of Formula I:

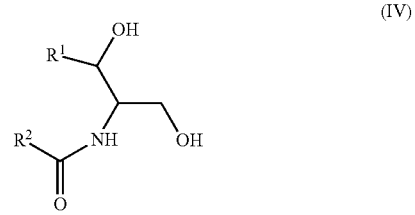

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms;

(b) determining in the biological sample from the subject the concentration of at least one ceramide of Formula II:

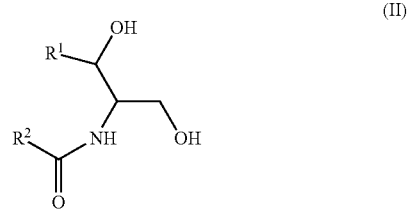

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms; and optionally (c) comparing the concentration of the at least one ceramide of Formula I and the concentration of the at least one ceramide of Formula II to a control sample.

In one embodiment of the aforementioned methods, the concentrations of at least 2, at least 3, at least 4, at least 5, or at least 6 ceramides of Formula I are determined. In another embodiment, the concentrations of at least 2, at least 3, at least 4, at least 5, or at least 6 ceramides of Formula II are determined. In yet another embodiment, the concentrations of at least 2, at least 3, at least 4, at least 5, or at least 6 ceramides of Formula I are determined and the concentrations of at least 2, at least 3, at least 4, at least 5, or at least 6 ceramides of Formula II are determined.

In one embodiment of the aforementioned methods, the concentrations of at least one of the following ceramides of Formula (II) are determined: Cer(d18:1/16:0), Cer(d18:1/18:0), and Cer(d18:1/24:1). In certain embodiments, the following Formula (II) ceramides or combinations thereof may be determined in the aforementioned detection methods:

| Formula (II)   | Formula (II)   | Formula (II)   |
|----------------|----------------|----------------|
| Cer(d18:1/16:0) | | |
| Cer(d18:1/18:0) | | |
| Cer(d18:1/24:1) | | |
| Cer(d18:1/16:0) | Cer(d18:1/18:0) | |
| Cer(d18:1/16:0) | Cer(d18:1/24:1) | |
| Cer(d18:1/18:0) | Cer(d18:1/24:1) | |
| Cer(d18:1/16:0) | Cer(d18:1/18:0) | Cer(d18:1/24:1) |

In another embodiment, the concentration of the following ceramide of Formula (I): Cer(d18:1/24:0) and the concentrations of at least one of the following ceramides of Formula (II): Cer(d18:1/16:0), Cer(d18:1/18:0), and Cer(d18:1/24:1) are determined. In certain embodiments, the concentrations of the following combinations of Formula (I) and Formula (II) ceramides may be determined in the aforementioned detection methods:

| Formula (I)   | Formula (II)   | Formula (II)   | Formula (II)   |
|---------------|----------------|----------------|----------------|
| Cer(d18:1/24:0) | Cer(d18:1/16:0) | | |
| Cer(d18:1/24:0) | Cer(d18:1/18:0) | | |
| Cer(d18:1/24:0) | Cer(d18:1/24:1) | | |
| Cer(d18:1/24:0) | Cer(d18:1/16:0) | Cer(d18:1/18:0) | |
| Cer(d18:1/24:0) | Cer(d18:1/16:0) | Cer(d18:1/24:1) | |
| Cer(d18:1/24:0) | Cer(d18:1/18:0) | Cer(d18:1/24:1) | |
| Cer(d18:1/24:0) | Cer(d18:1/16:0) | Cer(d18:1/18:0) | Cer(d18:1/24:1) |

In one embodiment of the aforementioned methods, the biological sample and the control sample comprise at least one isotope (e.g., deuterium) labelled ceramide of Formula I and at least one isotope (e.g., deuterium) labelled ceramide Formula II. In general, the isotope-labelled ceramide will be the same ceramide that is being detected in the biological sample. For example, if the concentrations of the following ceramides of Formula II: Cer(d18:1/16:0), Cer(d18:1/18:0), and Cer(d18:1/24:1) and the concentration of the following ceramide of Formula I: Cer(d18:1/24:0) are determined, the biological sample and the control sample will comprise an isotope-labelled Cer(d18:1/16:0), an isotope-labelled Cer(d18:1/18:0), an isotope-labelled Cer(d18:1/24:1), and an isotope-labelled Cer(d18:1/24:0).

In one embodiment of the aforementioned methods, the subject previously suffered from a cardiovascular disease event such as angina pectoris, myocardial infarction or stroke.

Also disclosed herein are methods of detecting in a biological sample obtained from a subject the concentration of at least one ceramide of Formula III and at least one ceramide of Formula IV, wherein the method comprises:

(a) determining in a biological sample obtained from the subject the concentration of at least one ceramide of Formula III:

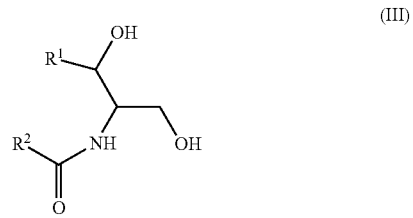

wherein $R^1$ is a mono-unsaturated alkyl chain having 13 carbon atoms or a di-unsaturated alkyl chain having 15 carbon atoms, and wherein $R^2$ is a saturated alkyl chain having 21-23 or 25 carbon atoms;

(b) determining in the biological sample from the subject the concentration of at least one ceramide of Formula IV:

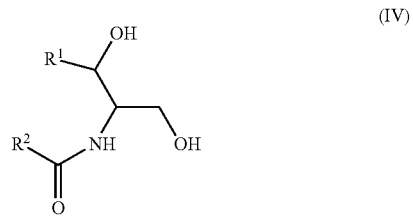

wherein $R^1$ is a mono-unsaturated alkyl chain having 13 carbon atoms and $R^2$ is a saturated alkyl chain having 15 or 17 carbon atoms, a mono-unsaturated alkyl chain having 23 carbon atoms, or a di-unsaturated alkyl chain having 23 carbon atoms; or wherein $R^1$ is a di-unsaturated alkyl chain having 15 carbon atoms and $R^2$ is a saturated alkyl chain having 15 or 17 carbon atoms, a mono-unsaturated alkyl chain having 21-23 carbon atoms, or a di-unsaturated alkyl chain having 23 carbon atoms; and optionally (c) comparing the concentration of the at least one ceramide of Formula III and the concentration of the at least one ceramide of Formula IV to a control sample.

In one embodiment of the aforementioned methods, the concentrations of at least 2, at least 3, at least 4, at least 5, or at least 6 ceramides of Formula III are determined. In another embodiment, the concentrations of at least 2, at least 3, at least 4, at least 5, or at least 6 ceramides of Formula IV are determined. In yet another embodiment, the concentrations of at least 2, at least 3, at least 4, at least 5, or at least 6 ceramides of Formula III are determined and the concentrations of at least 2, at least 3, at least 4, at least 5, or at least 6 ceramides of Formula IV are determined.

In one embodiment of the aforementioned methods, the biological sample and the control sample comprise at least one isotope (e.g., deuterium) labelled ceramide of Formula III and at least one isotope (e.g., deuterium) labelled ceramide Formula IV. In general, the isotope-labelled ceramide will be the same ceramide that is being detected in the biological sample.

In one embodiment of the aforementioned methods, the subject previously suffered from a cardiovascular disease event such as angina pectoris, myocardial infarction or stroke.

6. Measuring Ceramide Concentrations

In connection with all aspects and embodiments described and claimed herein, the determination of the ceramide concentration is typically performed using an assay. Collecting information on the concentration of a ceramide from the sample of a subject and, where appropriate, a corresponding control sample, can be performed with various chemical and high-resolution analytical techniques. Suitable analytical techniques include, but are not limited to, mass spectrometry and nuclear resonance spectroscopy. Any high-resolution technique capable of resolving individual ceramides or ceramide classes and providing structural information of the same can be used to collect the information on the ceramide marker in question, e.g., ceramide profile from the biological sample. Collecting the information on the ceramide marker with mass spectrometry (MS) is one of the preferred embodiments of the disclosed methods. The MS instrument can be coupled to a direct sample infusion method, such as a robotic nanoflow ion source device, or to a high performance separation method such as high performance liquid chromatography (HPLC) or ultra performance liquid chromatography (UPLC).

Other methods can be used or combined with MS and/or HPLC/UPLC to detect the ceramides of interest, including, for example, nuclear magnetic resonance spectroscopy, liquid chromatography, thin-layer chromatography, gas-chromatography, fluorescence spectroscopy or dual polarisation interferometry, and/or an immunoassay such as an ELISA. According to an alternative or further embodiment a ceramide in a sample can be detected and/or quantified using a binding moiety capable of specifically binding the ceramide. The binding moiety can include, for example, a member of a ligand-receptor pair, i.e., a pair of molecules capable of having a specific binding interaction. The binding moiety can also include, for example, a member of a specific binding pair, such as antibody-antigen, enzyme-substrate, nucleic acid-based ligands, other protein ligands, or other specific binding pairs known in the art.

In a preferred embodiment, the ceramide concentrations are measured using mass spectrometry (MS), wherein the MS instrument may be coupled to direct infusion methods or high performance separation methods such as HPLC or UPLC.

7. Sample Preparation and Isotope-Labelled Ceramides

In accordance with the methods described and claimed herein, both the biological sample from the subject and the control sample is preferably a blood sample, more preferably a blood plasma sample or a blood serum sample. The sample may also be a dried blood spot. It may also be a fraction of blood, blood plasma or blood serum, e.g., a lipid fraction extracted from the sample. The blood sample can be taken in connection with, for example, measuring the cholesterol levels in the patients. The collected blood sample can be prepared and serum or plasma can be separated with techniques well known to a person skilled in the art. Vena blood samples can be collected from patients using a needle and a BD Vacutainer® Plastic Tubes or Vacutainer® Plus Plastic Tubes (BD Vacutainer® SST' Tubes contain spray-coated silia and a polymer gel for serum separation). Serum can be separated from the collected blood sample, for example, by centrifugation at 1300 RCF for 10 min at room temperature and stored in small plastic tubes at −80° C. Plasma can be separated, for example, by centrifugation at 2,500×g at 4° C. for 5 minutes. A dried blood spot is prepared by placing a spot of blood on filter paper and allowing it to air dry.

Alternatively, both the sample from the subject and the control sample may also be a tissue sample, e.g., artery tissue, such as carotid artery tissue, or artery plaque material, such as carotid artery plaque material.

In one embodiment, the biological sample is spiked with a known amount of a isotope-labelled Group A, Group B, Group C, or Group D ceramide. Any isotope that can be used to detect the ceramides of interest can be used, including but not limited to hydrogen (e.g., deuterium), carbon, and oxygen isotopes. In a preferred embodiment, the biological sample is spiked with the isotope-labelled ceramide prior to lipid extraction. The isotope-labelled ceramide serves as an internal standard and is not a naturally occurring molecule. In a preferred embodiment, a deuterium label is used to produce deuterium-labelled ceramides, including, but not limited to N-palmitoyl-D-erythro-sphingosine-d7 (d18:1/16:0), N-stearoyl-D-erythro-sphingosine-d7 (d18:1/18:0), N-lignoceroyl-D-erythro-sphingosine-d7 (d18:1/24:0), and N-nervonoyl-D-erythro-sphingosine-d7 (Cer(d18:1/24:1)).

8. Controls

The ceramide levels in a biological sample obtained from a subject are compared to a control. The control may be a biological sample from a healthy individual. The control may also be a sample from CAD patient(s) with no history of major CVD events. It may also be a sample that represents a combination of samples from a generalized population of healthy individuals or a sample that represents a combination of samples from a CAD patient population with no history of major CVD events. The biological sample may be whole blood, blood serum, or blood plasma. It may also be a tissue sample. However, in a preferred embodiment, the biological sample is plasma or serum.

Alternatively, the control may be a set of data concerning a ceramide marker in accordance with the present invention, e.g., information on the concentration of ceramide(s) in accordance with the present invention in a sample when taken from a healthy individual, or in a combination of samples when taken from a generalized population of healthy individuals, or from CAD patient(s) with no history of major CVD events, or from a CAD patient population with no history of major CVD events. The information, and thus the corresponding set of data, may have been previously determined, calculated or extrapolated, or may have yet to be determined, calculated or extrapolated, or may also be taken from the literature.

In the methods of evaluating the effectiveness of a treatment, the control sample may be from a healthy individual, as discussed above, in which case, finding that the biological sample from the subject contains concentrations of at least one Group A (or Group C) ceramide and at least one Group B (or Group D) ceramide that are about the same as or equal to the control sample (not significantly different) indicates that the treatment was effective. Alternatively, the control sample can be obtained from a subject who is at risk to develop one or more CV complications, such as AMI, ACS, stroke, or CV death. In certain embodiments, the subject from whom the control sample is obtained is the same individual being treated, in which case a concentration of at least one Group A (or Group C) ceramide that is increased relative to the control sample and a concentration of at least one Group B (or Group D) ceramide that is decreased relative to the control sample, indicates that the treatment was effective.

9. Composition and Kits

Another aspect is a kit for predicting CV complications or for performing any of the methods disclosed herein, wherein the kit comprises at least one isotope (e.g., deuterium) labelled ceramide of Group A, B, C, or D, and optionally one or more reagents for performing the method. Also encompassed are compositions comprising at least one isotope (e.g., deuterium) labelled ceramide of Group A, B, C, or D.

In one embodiment, the composition or kit comprises at least one isotope (e.g., deuterium)-labelled ceramide of Formula I:

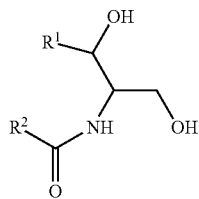

(I)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms.

In another embodiment, the composition or kit comprises at least one isotope (e.g., deuterium)-labelled ceramide of Formula II:

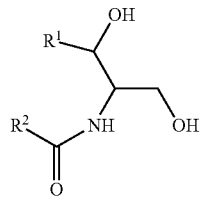

(II)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms.

For example, in certain embodiments, the composition or kit comprises one of the following isotope (e.g., deuterium)-labelled ceramides of Formula II or combinations thereof:

| Formula (II) | Formula (II) | Formula (II) |
|---|---|---|
| Cer(d18:1/16:0) | | |
| Cer(d18:1/18:0) | | |
| Cer(d18:1/24:1) | | |
| Cer(d18:1/16:0) | Cer(d18:1/18:0) | |
| Cer(d18:1/16:0) | Cer(d18:1/24:1) | |
| Cer(d18:1/18:0) | Cer(d18:1/24:1) | |
| Cer(d18:1/16:0) | Cer(d18:1/18:0) | Cer(d18:1/24:1) |

In another embodiment, the kit or composition comprises at least one isotope (e.g., deuterium)-labelled ceramide of Formula I and at least one isotope (e.g., deuterium)-labelled ceramide of Formula II. In other embodiments, the kit or composition comprises at least 2, at least 3, at least 4, at least 5, or at least 6 isotope (e.g., deuterium)-labelled ceramides of Formula I and/or at least 2, at least 3, at least 4, at least 5, or at least 6 isotope (e.g., deuterium)-labelled ceramides of Formula II.

For example, in certain embodiments, the composition or kit comprises the following combinations of isotope (e.g., deuterium)-labelled ceramides of Formula (I) and Formula II:

| Formula (I) | Formula (II) | Formula (II) | Formula (II) |
|---|---|---|---|
| Cer(d18:1/24:0) | Cer(d18:1/16:0) | | |
| Cer(d18:1/24:0) | Cer(d18:1/18:0) | | |
| Cer(d18:1/24:0) | Cer(d18:1/24:1) | | |
| Cer(d18:1/24:0) | Cer(d18:1/16:0) | Cer(d18:1/18:0) | |
| Cer(d18:1/24:0) | Cer(d18:1/16:0) | Cer(d18:1/24:1) | |
| Cer(d18:1/24:0) | Cer(d18:1/18:0) | Cer(d18:1/24:1) | |
| Cer(d18:1/24:0) | Cer(d18:1/16:0) | Cer(d18:1/18:0) | Cer(d18:1/24:1) |

In other embodiments, the composition or kit comprises at least one isotope (e.g., deuterium)-labelled ceramide of Formula III:

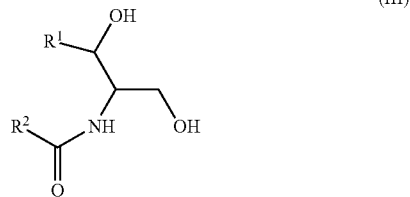

(III)

wherein $R^1$ is a mono-unsaturated alkyl chain having 13 carbon atoms or a di-unsaturated alkyl chain having 15 carbon atoms, and wherein $R^2$ is a saturated alkyl chain having 21-23 or 25 carbon atoms.

Another aspect is directed to a composition or kit comprising at least one isotope (e.g., deuterium)-labelled ceramide of Formula IV:

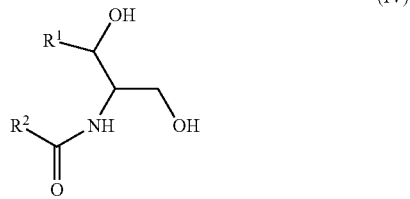

(IV)

wherein $R^1$ is a mono-unsaturated alkyl chain having 13 carbon atoms and $R^2$ is a saturated alkyl chain having 15 or 17 carbon atoms, a mono-unsaturated alkyl chain having 23 carbon atoms, or a di-unsaturated alkyl chain having 23 carbon atoms; or wherein $R^1$ is a di-unsaturated alkyl chain having 15 carbon atoms and $R^2$ is a saturated alkyl chain having 15 or 17 carbon atoms, a mono-unsaturated alkyl chain having 21-23 carbon atoms, or a di-unsaturated alkyl chain having 23 carbon atoms.

In another embodiment, the kit or composition comprises at least one isotope (e.g., deuterium)-labelled ceramide of Formula III and at least one isotope (e.g., deuterium)-labelled ceramide of Formula IV. In other embodiments, the kit or composition comprises at least 2, at least 3, at least 4, at least 5, or at least 6 isotope (e.g., deuterium)-labelled ceramides of Formula III and/or at least 2, at least 3, at least 4, at least 5, or at least 6 isotope (e.g., deuterium)-labelled ceramides of Formula IV. The composition may further comprise a solution, such as distilled water, a buffered solution, or other appropriate solvent.

All kits disclosed herein may be accompanied by instructions to use them for predicting a CV complication, such as AMI, ACS, stroke, and CV death.

10. Computer-Implemented Diagnostic Methods

In accordance with all aspects and embodiments disclosed herein, the methods provided may be computer-implemented.

In one embodiment, any of the computer-implemented methods of the invention may further comprise the steps of (i) obtaining by at least one processor information reflecting the concentration of at least one Group A ceramide and at least one Group B ceramide (or at least one Group C ceramide and at least one Group D ceramide) in the biological sample; and (ii) outputting in user readable format the concentration of at least one Group A ceramide and at least one Group B ceramide (or at least one Group C ceramide and at least one Group D ceramide) in the biological sample.

In another embodiment, the computer-implemented methods may further comprise a step of determining by at least one processor a percentage difference between a control and the concentration of at least one Group A ceramide and at least one Group B ceramide (or at least one Group C ceramide and at least one Group D ceramide) in the biological sample; and a step of outputting in user readable format the percentage difference obtained in the determining step (iii).

In yet another embodiment, the computer-implemented methods may further comprise a step of determining whether a subject is at risk to develop one or more CV complications based on the percentage difference obtained in the outputting step.

In one embodiment of the computer-implemented methods, the at least one Group A ceramide comprises Cer(d18:1/24:0) and the at least one Group B ceramide comprises Cer(d18:1/16:0), Cer(d18:1/18:0), and Cer(d18:1/24:1).

In embodiments as shown in FIG. 4, computer system 106 may include one or more processors 110 coupled to random access memory operating under control of or in conjunction with an operating system. The processor(s) 110 in embodiments may be included in one or more servers, clusters, or other computers or hardware resources, or may be implemented using cloud-based resources. The operating system may be, for example, a distribution of the Linux™ operating system, the Unix™ operating system, or other open-source or proprietary operating system or platform. Processor(s) 110 may communicate with data store 112, such as a database stored on a hard drive or drive array, to access or store program instructions other data.

Processor(s) 110 may further communicate via a network interface 108, which in turn may communicate via the one or more networks 104, such as the Internet or other public or private networks, such that a query or other request may be received from client 102, or other device or service. Additionally, processor(s) 110 may utilize network interface 108 to send information, instructions, workflows query partial workflows, or other data to a user via the one or more networks 104. Network interface 104 may include or be communicatively coupled to one or more servers. Client 102 may be, e.g., a personal computer coupled to the internet.

Processor(s) 110 may, in general, be programmed or configured to execute control logic and control operations to implement methods disclosed herein. Processors 110 may be further communicatively coupled (i.e., coupled by way of a communication channel) to co-processors 114. Co-processors 114 can be dedicated hardware and/or firmware components configured to execute the methods disclosed herein. Thus, the methods disclosed herein can be executed by processor 110 and/or co-processors 114.

Other configurations of computer system 106, associated network connections, and other hardware, software, and service resources are possible.

The following Examples further define and describe embodiments herein.

EXAMPLES

Example 1

Study patients.

The Corogene study is a prospective cohort study where 5000 consecutive Finnish patients were assigned to diagnostic coronary angiogram in the region of Helsinki University Central Hospital. In this study, 436 CAD patients with >50% stenosis in at least one coronary artery were analyzed. In this nested case-control study, one control subject was matched for each case. The cases were CAD patients that died due to CV reasons during an average follow-up of 2.5 years. The matching controls were CAD patients, who did not die during the follow-up for any cause. The matching criteria included: Age, gender, body mass index, statin use, smoking and type 2 diabetes.

Analytical Methods.

For quantification, ceramides were extracted using a modified Folch lipid extraction performed on a Hamilton Microlab Star robot, as described in Jung H R et al., High throughput quantitative molecular lipidomics. Biochim Biophys Acta. 2011 November; 1811(11):925-34, which is hereby incorporated by reference in its entirety. Samples were spiked with known amounts of non-endogeneous synthetic internal standards. After lipid extraction, samples were reconstituted in chloroform:methanol (1:2, v/v) and a synthetic external standard was post-extract spiked to the extracts. The extracts were stored at −20° C. prior to MS analysis.

Ceramides were analyzed on a hybrid triple quadrupole/linear ion trap mass spectrometer (5500 QTRAP) equipped with an ultra high pressure liquid chromatography (UHPLC) system (Eksigent ultraLC 100 system) using multiple reaction monitoring (MRM)-based method in negative ion mode based on the description by Sullards M C et al., Structure-specific, quantitative methods for analysis of sphingolipids by liquid chromatography-tandem mass spectrometry: "inside-out" sphingolipidomics. Methods Enzymol. 2007; 432:83-115.

The LC-MRM analysis was supplemented to include the precise measurement of new groups of (d16:1 and d18:2) ceramides not previously known to exist in human plasma (see Table 1). Their existence was verified in human plasma by sequential MS/MS analyses and retention time. In MS/MS, the identification was confirmed by the selective sphingosine fragment ions produced by the expected molecular ions, e.g. m/z of 236.25 corresponding to d16:1, m/z of 262.25 corresponding to d18:2. Further, this was complemented by the systematic retention time shift. The characteristic shifts confirmed the identity of the novel ceramide species. Their existence and ability to perform as biomarkers for the purpose described in this application was surprising and unexpected.

Masses and counts of detected peaks by mass spectrometry were converted into a list of corresponding lipid names and concentrations. Calibration lines were generated to determine the dynamic quantification range for each lipid class monitored, e.g., the quantification limits. Internal standards were used for quantifying endogenous lipid species. Calibration lines were used to determine the quantification limits of the method.

Stringent cutoff was applied for separating background noise from actual lipid peaks. Each sample was controlled and only accepted when fulfilling the acceptance criteria. Masses and counts of detected peaks were converted into a list of corresponding lipid names. Lipids were normalized to their respective internal standard and sample volume to retrieve their concentrations.

Targeted Ceramide Quantification of Cer(d18:1/16:0), Cer(d18:1/18:0), Cer(d18:1/24:0), and Cer(d18:1/24:1) molecules.

Ceramides were extracted using a modified Folch lipid extraction performed on a Hamilton Microlab Star robot, as described in Jung et al. For quantification of the specific combination of Cer(d18:1/16:0), Cer(d18:1/18:0), Cer(d18:1/24:0), and Cer(d18:1/24:1), the biological samples were spiked with a known amount of the following deuterium-labelled internal standards prior to lipid extraction: N-palmitoyl-D-erythro-sphingosine-d7 (Cer(d18:1/16:0)), N-stearoyl-D-erythro-sphingosine-d7 (Cer(d18:1/18:0)), N-lignoceroyl-D-erythro-sphingosine-d7 (Cer(d18:1/24:0)), and N-nervonoyl-D-erythro-sphingosine-d7 (Cer(d18:1/24:1)). Calibration line standards were made in solution as no suitable lipid free matrix was available. Known amount of analyte and stable isotope-labelled internal standards was added to chloroform:methanol (1:2, v/v) to make the calibration line points.

LC-MS/MS was conducted on hybrid triple quadrupole/linear ion trap mass spectrometer (QTRAP 5500) equipped with an ultra-high pressure liquid chromatography (UHPLC) system (Eksigent ultraLC 100 system) using multiple reaction monitoring (MRM) based method in positive ion mode.

Sample extract (5 µL) was loaded on Waters Acquity BEH C18, 2.1×50 mm id. 1.7 µm connected to Waters Acquity BEH C18, 1.7 µm VanGuard Pre-Column at column temperature of 60° C. The mobile phase A consisted of 10 mM ammonium acetate in HPLC grade water with 0.1% formic acid and mobile phase B. The flow rate of 0.5 µL/min with the following gradient: 0.0-0.5 min, 85% B; 0.5-1.5 min, 85 to 100 & B; 1.5-4 min, 100% B; 4.10-5 min, 85% B. The source temperature was set to 300° C.; ion spray was 5000V; declustering potential 30 V; entrance potential was 10; gas 1 and gas 2 setting were 50 and 30. Dwell time for each scan was 25 msec and collision energy was set at 40 V. Total acquisition time was 4.5 min.

Data was acquired with Analyse software (version 1.6) and processed with MultiQuant (version 3.0). Calibration line curves were constructed by plotting the peak area ratio of analyte/internal standards against the actual concentration using, for example, weighted of $1/x^2$ for Cer(d18:1/16:0) and Cer(d18:1/18:0) and $1/y^2$ for Cer(d18:1/24:1) and Cer(d18:1/24:1). Peak area ratio of the samples were read off the calibration lines.

The 7 deuterium in the sphingosine backbone of the labelled standards provide a mass shift of 7 Da in their sphingosine fragment ions upon MS/MS of the parent ion. The mass difference of the parent ion including sphingosine fragment ion in the MRM analysis of the endogenous and internal standard will be therefore be 7 Da respectively, e.g. MRM transitions of Cer d18:1/16:0 and D7-Cer 18:1/16:0 are 538.5/264.2 and 545.5/271.2.

The identical analytical behavior, such as extraction recovery, ionization and retention time, of the internal standard and corresponding endogenous species including the mass shift, facilitates the precise measurement and quantification. The peak area ratio of the endogeneous ceramide to its internal standard in samples is read off a calibration line to provide the precise quantity of the endogenous ceramide in samples. The calibration line is obtained by analyzing a dilution series of the endogeneous ceramides mixed with a fixed amount of the deuterated standards by LC-MRM as described.

The deuterium labelled internal standards were specifically manufactured for this assay. Thus, the absolute quantification of these specific deuterium-labelled ceramides has not been performed previously.

Statistical Methods.

Odds ratio quantitatively describes the association between the presence/absence of a described cardiovascular outcome event and the presence/absence of no event for stable CAD individuals in the population. The odds ratio per standard deviation (OR per SD) quantifies the odds of positive prediction in case group divided by the odds of positive prediction in the control group as a response to a one standard deviation change in the variable. Quartile odds ratios (OR 2-4) quantify the ratio of positive outcomes to negative outcomes in different quartiles relative to these ratios in the first quartile. Area under the receiver operating characteristic curve (AUC) describes the overall predictive performance of the marker. Its values are between 0 and 1, with 0.5 corresponding to random, 50/50 (e.g., coin flipping), predictions of the outcome, and higher values indicating better prediction accuracy in terms of sensitivity (sens) and specificity (spec). Mean relative change (MRC %) is calculated as the difference between the mean values of the ceramide concentrations in the case and control groups divided by the mean value in the control group. P-value is calculated using Student's t-test on log-transformed data. Also false discover rate q-value estimates are calculated. These q-values estimate the percentage of false positive findings among all the markers whose p-value is smaller than the p-value of the corresponding marker.

A logistic regression model for explaining case versus control grouping using the lipid concentrations (either single or two lipids in the model, corresponding to single marker versus two marker diagnostic model) was fit to the Corogene study population. A likelihood ratio test with deviance statistics was estimated. Deviance measurements are commonly used to compare models. Deviance is a quality of fit statistic for a model that represents a measure of the lack of fit between model and data. In general, the larger the deviance, the poorer the fit of the data to the model. The deviance is usually not interpreted directly, but rather compared to deviance(s) from other models fitted to the same data. See e.g., Nelder, J. A.; Wedderburn, (1972). "Generalized Linear Models." *Journal of the Royal Statistical Society. Series A (General)* 135 (3): 370-384.

The likelihood ratio test can be applied for nested models, that is, for two models, one with a larger number of variables and the other with a subset of variables of the larger model. The deviance statistics follows approximately Chi-square distribution from which the statistical significance can be estimated. Here $p<0.05$ has been used as a threshold for significant difference. If $p>0.05$, the two models do not significantly differ from each other in terms of discriminating cases from controls. In contrast, when $p<0.05$, the model with larger number of variables outperforms the smaller model. Likelihood ratio test for nested models using deviance statistics is an established method for comparing models with different number of variables.

Results.

In the example study, the ceramide concentrations in CAD patients with CV events during a follow-up were compared to control subjects without events. FIGS. 1 and 2 show the mean relative changes/differences (the difference of case versus control group means divided by the mean concentration of the control group) of ten Group A and ten Group B ceramide species with the lowest Student's t-test p-values. These demonstrate the power (e.g., better odds ratios (AUC), or sensitivity and specificity, lower p values) of individual ceramide species to discriminate high-risk patients (with forthcoming CV events) from control patients, as most of the ceramide species in either Group A or Group B discriminate cases and control groups with $p<0.05$.

Ceramides that do not fall within either Group A or Group B were also analyzed and it was found, in general, that such ceramides do not discriminate cases from controls with $p<0.05$ by Student's t-test on log-transformed concentration estimates, as shown in FIG. 3.

Deviance statistics were used to analyze various combinations of ceramide concentrations in patients from the Corogene study and, in particular, CAD patients with CV events during a follow-up as compared to control subjects without events. The results of the deviance statistics are summarized in Model Comparisons 1-9.

Example 2

Model Comparison 1.

In Model Comparison 1, a single ceramide species (either Group A or B) was compared to a combination of two ceramides, one from Group A and the other from Group B. In Model Comparison 1, the fact that Pr(>Chi)<0.05 for the combined two marker model against either of the single marker models, indicates that the discriminatory power of the combined model is significantly better than that of the single marker models, as shown in Table 4 below.

TABLE 4

| Model Comparison 1 | | | |
|---|---|---|---|
| Cer(d18:1/16:0) (B) vs. Cer(d18:1/16:0) (B) + Cer(d18:1/24:0) (A) | | Cer(d18:1/24:0) (A) vs. Cer(d18:1/24:0) (A) + Cer(d18:1/16:0) (B) | |
| Deviance | Pr(>Chi) | Deviance | Pr(>Chi) |
| −45.2 | $1.80*10^{-11}$ | −77.0 | $2.20*10^{-16}$ |

Example 3

Model Comparison 2.

There is no particular reason to restrict the discriminatory model to a combination of only two ceramides. However, for practical purposes and for cost limiting reasons, it is preferable to use as few ceramides as possible. Thus, one has to weigh the benefit of increasing sensitivity and specificity against the additional cost of analyzing more molecular lipid species. In Model Comparison 2, a model with two ceramide species was compared against a model with three ceramide species, where the three ceramide markers included at least one Group A ceramide and at least one Group B ceramide. In Model Comparison 2, Pr(>Chi)<0.05 for the combined three marker model against either of the double marker models indicates that the discriminatory power of the three marker model is significantly better than that of the double marker models, as shown in Table 5.

TABLE 5

| Model Comparison 2 | | | |
|---|---|---|---|
| Cer(d18:0/18:0) (B) + Cer(d18:1/23:1) (B) vs. Cer(d18:0/18:0) (B) + Cer(d18:1/23:1) (B) + Cer(d18:2/25:0) (A) | | Cer(d18:0/18:0) (B) + Cer(d18:2/25:0) (A) vs. Cer(d18:0/18:0) (B) + Cer(d18:2/25:0) (A) + Cer(d18:1/23:1) (B) | |
| Deviance | Pr(>Chi) | Deviance | Pr(>Chi) |
| −42.4 | $7.30*10^{-11}$ | −33.3 | $7.70*10^{-09}$ |

Example 4

Model Comparison 3:

Increasing the number of ceramide species in the model does not necessarily mean that a better model will result. As an example of this, Model Comparison 3 shows a three ceramide model that is not better than a two ceramide model. In this case, a combination of two ceramides from Group B were compared to three ceramides from Group B. In Model Comparison 3, Pr(>Chi)>0.05 for the combined three marker model as compared to a two marker model, indicates that the discriminatory power of the three marker model is not significantly better than that of the double marker model, as shown in Table 6.

TABLE 6

| Model Comparison 3 Cer(d18:1/23:1) (B) + Cer(d18:1/18:0) (B) vs. Cer(d18:1/23:1) (B) + Cer(d18:0/18:0) (B) + Cer(d18:1/18:0) (B) | |
|---|---|
| Deviance | Pr(>Chi) |
| −2.3 | 0.1321 |

Thus, Model Comparison 3 demonstrates that merely increasing the number of ceramides does not result in an improved model performance. Rather, the combined ceramides should be selected according to the guidance provided in this application, with at least one ceramide of Group A and at least one ceramide of Group B.

Example 5

Model Comparison 4.

An interesting combination of ceramide species is shown in Model Comparison 4. This combination includes three Group B ceramides: Cer(d18:1/16:0), Cer(d18:1/18:0), and Cer(d18:1/24:1); and one Group A ceramide: Cer(d18:1/24:0). This particular combination appears systematically in all analyzed study populations. In addition, the ceramide species in Model Comparison 4 are abundant in human serum or plasma samples when compared to the abundance of ceramide species in general. The model which combines the four ceramide species outperforms models with its single components in all cases (all Pr(>Chi)<0.05), as shown in Table 7.

TABLE 7

| Model Comparison 4 Cer(d18:1/16:0) (B) + Cer(d18:1/18:0) (B) + Cer(d18:1/24:0) (A) + Cer(d18:1/24:1) (B) | | |
|---|---|---|
| | Deviance | Pr(>Chi) |
| vs. Cer(d18:1/16:0) | −66.3 | $2.69*10^{-14}$ |
| vs. Cer(d18:1/18:0) | −59.9 | $6.06*10^{-13}$ |
| vs. Cer(d18:1/24:0) | −98.1 | $2.20*10^{-16}$ |
| vs. Cer(d18:1/24:1) | −86.4 | $2.20*10^{-16}$ |

Example 6

Model Comparisons 5-7.

There may be a general perception that the diagnostic power of a combination of biomarkers will increase as the number of biomarkers analyzed increases. As shown in Model Comparison 3, however, this perception does not necessarily play out with ceramide biomarkers in the context of predicting CV complications. Model Comparisons 5-7 further demonstrate that simply increasing the number of ceramide species in the model, without applying the rule of selecting at least one Group A ceramide and at least one Group B ceramide, does not improve the model performance. Thus, Model Comparisons 5-7 demonstrate the lack of diagnostic power for randomly selecting ceramides as compared to selecting ceramides based on the newly identified rule of selecting at least one Group A ceramide and at least one Group B ceramide.

In Model Comparison 5, combinations of ceramides that do not fall within Group A or Group B were analyzed. In Table 8, 15 model comparisons are shown with their deviance statistics and Chi-square p-value estimates (with p<0.05 denoting significant difference between the models). In each model comparison, random combinations of ceramides that do not include at least one Group A ceramide and at least one Group B ceramide were compared. In all 15 examples with varying model sizes, the p-value for the deviance statistics is greater than 0.05, which means that the model with more non AB ceramides is not significantly better in discriminating the case-control grouping as compared to the model with fewer ceramides.

TABLE 8

| Model Comparison 5 | | |
|---|---|---|
| Comparison of combinations outside groups A and B | Deviance | P-value |
| Cer(d18:1/20:0) + Cer(d18:1/21:0) + Cer(d18:1/26:2) + Cer(d18:0/20:0) vs Cer(d18:1/20:0) + Cer(d18:1/26:2) + Cer(d18:0/20:0) | $-8.08*10^{-05}$ | 0.992826 |
| Cer(d18:1/21:0) + Cer(d18:1/20:0) + Cer(d18:1/26:2) vs Cer(d18:1/20:0) + Cer(d18:1/26:2) | −0.00879 | 0.925325 |
| Cer(d18:1/20:0) + Cer(d18:1/21:0) vs Cer(d18:1/20:0) | −0.05299 | 0.817934 |
| Cer(d18:0/20:0) + Cer(d18:1/21:0) + Cer(d18:1/20:0) vs Cer(d18:0/20:0) + Cer(d18:1/20:0) | −0.11153 | 0.738412 |
| Cer(d18:1/20:0) + Cer(d18:1/21:0) + Cer(d18:1/26:2) + Cer(d18:0/20:0) vs Cer(d18:1/20:0) + Cer(d18:1/21:0) + Cer(d18:1/26:2) | −0.14819 | 0.700267 |
| Cer(d18:1/20:0) + Cer(d18:0/20:0) + Cer(d18:1/26:2) vs Cer(d18:1/20:0) + Cer(d18:1/26:2) | −0.1569 | 0.692029 |
| Cer(d18:1/20:0) + Cer(d18:0/20:0) vs Cer(d18:1/20:0) | −0.2269 | 0.63383 |

TABLE 8-continued

| Model Comparison 5 | | |
| --- | --- | --- |
| Comparison of combinations outside groups A and B | Deviance | P-value |
| Cer(d18:0/20:0) + Cer(d18:1/21:0) + Cer(d18:1/20:0) vs Cer(d18:1/21:0) + Cer(d18:1/20:0) | −0.28544 | 0.59316 |
| Cer(d18:1/26:2) + Cer(d18:0/20:0) + Cer(d18:1/21:0) vs Cer(d18:1/26:2) + Cer(d18:0/20:0) | −0.59528 | 0.440384 |
| Cer(d18:1/26:2) + Cer(d18:1/21:0) vs Cer(d18:1/26:2) | −0.80246 | 0.370359 |
| Cer(d18:1/26:2) + Cer(d18:0/20:0) + Cer(d18:1/21:0) vs Cer(d18:1/26:2) + Cer(d18:1/21:0) | −0.99255 | 0.319119 |
| Cer(d18:1/20:0) + Cer(d18:1/21:0) + Cer(d18:1/26:2) + Cer(d18:0/20:0) vs Cer(d18:1/21:0) + Cer(d18:1/26:2) + Cer(d18:0/20:0) | −0.99354 | 0.318878 |
| Cer(d18:1/26:2) + Cer(d18:0/20:0) vs Cer(d18:1/26:2) | −1.19973 | 0.273375 |
| Cer(d18:1/20:0) + Cer(d18:0/20:0) + Cer(d18:1/26:2) vs Cer(d18:0/20:0) + Cer(d18:1/26:2) | −1.58874 | 0.207506 |
| Cer(d18:1/21:0) + Cer(d18:1/20:0) + Cer(d18:1/26:2) vs Cer(d18:1/21:0) + Cer(d18:1/26:2) | −1.8379 | 0.175197 |

In Model Comparison 6, random combinations of Group A ceramides (without at least one Group B ceramide) were compared. In Table 9, 15 model comparisons are shown with their deviance statistics and Chi-square p-value estimates (with p<0.05 denoting significant difference between the models). In all 15 examples with varying model sizes, the p-value for the deviance statistics is greater than 0.05 which means that the model with more Group A ceramides is not significantly better in discriminating the case-control grouping as compared to the model with fewer Group A ceramides.

TABLE 9

| Model Comparison 6 | | |
| --- | --- | --- |
| Comparison of combinations from Group A | Deviance | P-value |
| Cer(d16:1/23:0) + Cer(d18:2/26:0) vs Cer(d18:2/26:0) | $-1.22*10^{-05}$ | 0.997211 |
| Cer(d18:1/25:0) + Cer(d18:2/22:0) + Cer(d18:1/24:0) + Cer(d16:1/26:0) + Cer(d18:2/23:0) vs Cer(d18:1/25:0) + Cer(d18:2/22:0) + Cer(d16:1/26:0) + Cer(d18:2/23:0) | −0.00016 | 0.990018 |
| Cer(d18:1/24:0) + Cer(d18:1/26:0) + Cer(d18:0/24:0) + Cer(d18:0/25:0) + Cer(d18:2/22:0) vs Cer(d18:1/24:0) + Cer(d18:1/26:0) + Cer(d18:0/24:0) + Cer(d18:0/25:0) | −0.00027 | 0.986808 |
| Cer(d18:2/14:0) + Cer(d18:1/25:0) + Cer(d18:2/26:0) vs Cer(d18:1/25:0) + Cer(d18:2/26:0) | −0.00052 | 0.981846 |
| Cer(d18:2/26:0) + Cer(d18:1/24:0) + Cer(d18:2/23:0) + Cer(d18:1/26:0) vs Cer(d18:2/26:0) + Cer(d18:1/24:0) + Cer(d18:1/26:0) | −0.00124 | 0.971963 |
| Cer(d18:0/24:0) + Cer(d18:2/24:0) + Cer(d16:1/26:0) + Cer(d16:1/24:0) vs Cer(d18:0/24:0) + Cer(d18:2/24:0) + Cer(d16:1/26:0) | −0.00241 | 0.960812 |
| Cer(d16:1/22:0) + Cer(d18:1/24:0) + Cer(d18:2/26:0) + Cer(d18:2/24:0) + Cer(d18:1/23:0) vs Cer(d18:1/24:0) + Cer(d18:2/26:0) + Cer(d18:2/24:0) + Cer(d18:1/23:0) | −0.00382 | 0.950741 |
| Cer(d18:2/26:0) + Cer(d16:1/26:0) + Cer(d18:2/24:0) + Cer(d16:1/24:0) vs Cer(d18:2/26:0) + Cer(d16:1/26:0) + Cer(d18:2/24:0) + Cer(d16:1/24:0) | −0.00462 | 0.945827 |
| Cer(d16:1/26:0) + Cer(d18:2/26:0) + Cer(d18:2/14:0) + Cer(d18:2/24:0) vs Cer(d16:1/26:0) + Cer(d18:2/26:0) + Cer(d18:2/24:0) | −0.0068 | 0.934272 |
| Cer(d16:1/23:0) + Cer(d18:2/25:0) + Cer(d18:1/25:0) + Cer(d18:2/24:0) vs Cer(d16:1/23:0) + Cer(d18:2/25:0) + Cer(d18:2/24:0) | −0.00743 | 0.931329 |
| Cer(d18:2/23:0) + Cer(d16:1/22:0) + Cer(d18:1/24:0) + Cer(d16:1/26:0) + Cer(d18:2/26:0) vs Cer(d18:2/23:0) + Cer(d16:1/22:0) + Cer(d16:1/26:0) + Cer(d18:2/26:0) | −0.01043 | 0.918649 |
| Cer(d18:2/24:0) + Cer(d16:1/26:0) + Cer(d18:0/25:0) + Cer(d18:2/22:0) vs Cer(d18:2/24:0) + Cer(d18:0/25:0) + Cer(d18:2/22:0) | −0.01459 | 0.903867 |
| Cer(d18:2/26:0) + Cer(d18:2/14:0) + Cer(d18:1/24:0) + Cer(d18:1/26:0) + Cer(d16:1/22:0) vs Cer(d18:2/26:0) + Cer(d18:1/24:0) + Cer(d18:1/26:0) + Cer(d16:1/22:0) | −0.0147 | 0.903505 |
| Cer(d16:1/24:0) + Cer(d18:2/24:0) + Cer(d18:2/22:0) + Cer(d16:1/26:0) vs Cer(d16:1/24:0) + Cer(d18:2/24:0) + Cer(d18:2/22:0) | −0.01491 | 0.902817 |
| Cer(d18:1/26:0) + Cer(d16:1/23:0) + Cer(d18:2/14:0) + Cer(d18:2/23:0) vs Cer(d18:1/26:0) + Cer(d18:2/14:0) + Cer(d18:2/23:0) | −0.01718 | 0.895724 |

In Model Comparison 7, random combinations of Group B ceramides (without at least one Group A ceramide) were compared. In Table 10, 15 model comparisons are shown with their deviance statistics and Chi-square p-value estimates (with p<0.05 denoting significant difference between the models). In all 15 examples with varying model sizes, the p-value for the deviance statistics is greater than 0.05 which means that the model with more Group B ceramides is not significantly better in discriminating the case-control grouping as compared to the model with fewer Group B ceramides.

TABLE 10

Model Comparison 7

| Comparison of combinations from Group B | Deviance | P-value |
|---|---|---|
| Cer(d16:1/16:0) + Cer(d18:1/24:1) + Cer(d18:0/18:0) + Cer(d18:0/24:2) + Cer(d18:1/16:0) vs Cer(d16:1/16:0) + Cer(d18:1/24:1) + Cer(d18:0/18:0) + Cer(d18:1/16:0) | $-7.10*10^{-06}$ | 0.997874 |
| Cer(d18:1/23:1) + Cer(d18:0/24:2) vs Cer(d18:1/23:1) | $-7.20*10^{-06}$ | 0.997859 |
| Cer(d18:2/22:1) + Cer(d16:1/16:0) + Cer(d18:0/18:0) + Cer(d18:1/16:0) + Cer(d18:0/24:2) vs Cer(d18:2/22:1) + Cer(d16:1/16:0) + Cer(d18:0/18:0) + Cer(d18:1/16:0) | $-7.08*10^{-05}$ | 0.993284 |
| Cer(d18:1/24:1) + Cer(d18:2/24:2) + Cer(d18:0/24:1) + Cer(d18:1/23:1) + Cer(d18:1/18:0) vs Cer(d18:1/24:1) + Cer(d18:2/24:2) + Cer(d18:1/23:1) + Cer(d18:1/18:0) | $-0.00025$ | 0.98747 |
| Cer(d18:1/23:1) + Cer(d18:1/16:0) + Cer(d18:1/24:2) + Cer(d18:1/18:0) + Cer(d18:0/24:1) vs Cer(d18:1/16:0) + Cer(d18:1/24:2) + Cer(d18:1/18:0) + Cer(d18:0/24:1) | $-0.00034$ | 0.985232 |
| Cer(d16:1/16:0) + Cer(d18:2/18:0) + Cer(d18:0/16:0) + Cer(d18:0/24:2) vs Cer(d18:2/18:0) + Cer(d18:0/16:0) + Cer(d18:0/24:2) | $-0.00047$ | 0.982751 |
| Cer(d18:0/16:0) + Cer(d18:2/24:2) + Cer(d16:1/16:0) + Cer(d18:0/24:2) + Cer(d18:1/24:1) vs Cer(d18:0/16:0) + Cer(d18:2/24:2) + Cer(d16:1/16:0) + Cer(d18:1/24:1) | $-0.00084$ | 0.97694 |
| Cer(d18:1/22:1) + Cer(d18:1/23:1) + Cer(d16:1/16:0) + Cer(d18:2/24:2) vs Cer(d18:1/22:1) + Cer(d18:1/23:1) + Cer(d18:2/24:2) | $-0.00098$ | 0.975028 |
| Cer(d18:0/16:0) + Cer(d18:2/18:0) + Cer(d18:1/24:1) + Cer(d18:0/24:1) vs Cer(d18:0/16:0) + Cer(d18:1/24:1) + Cer(d18:0/24:1) | $-0.00129$ | 0.971348 |
| Cer(d16:1/16:0) + Cer(d18:1/22:1) + Cer(d18:1/23:1) vs Cer(d18:1/22:1) + Cer(d18:1/23:1) | $-0.00141$ | 0.970081 |
| Cer(d18:2/16:0) + Cer(d18:0/24:2) + Cer(d18:2/24:2) + Cer(d18:0/18:0) + Cer(d18:2/22:1) vs Cer(d18:2/16:0) + Cer(d18:0/24:2) + Cer(d18:2/24:2) + Cer(d18:0/18:0) | $-0.00188$ | 0.965379 |
| Cer(d18:2/24:2) + Cer(d18:1/18:0) + Cer(d18:2/22:1) + Cer(d18:2/16:0) + Cer(d18:1/23:1) vs Cer(d18:1/18:0) + Cer(d18:2/22:1) + Cer(d18:2/16:0) + Cer(d18:1/23:1) | $-0.00229$ | 0.961812 |
| Cer(d18:2/18:0) + Cer(d16:1/16:0) + Cer(d18:0/18:0) + Cer(d18:0/16:0) + Cer(d18:1/24:1) vs Cer(d18:2/18:0) + Cer(d18:0/18:0) + Cer(d18:0/16:0) + Cer(d18:1/24:1) | $-0.00321$ | 0.9548 |
| Cer(d16:1/16:0) + Cer(d18:2/18:0) + Cer(d18:0/16:0) + Cer(d18:0/24:2) vs Cer(d16:1/16:0) + Cer(d18:2/18:0) + Cer(d18:0/16:0) | $-0.00378$ | 0.950985 |
| Cer(d16:1/16:0) + Cer(d18:0/24:1) + Cer(d18:0/16:0) + Cer(d18:1/22:1) vs Cer(d18:0/24:1) + Cer(d18:0/16:0) + Cer(d18:1/22:1) | $-0.00529$ | 0.941997 |

Example 7

Model Comparisons 8-9.

Model Comparisons 8-9 supplement Model Comparisons 1, 2, and 4, comparing combinations of at least one Group A and at least one Group B ceramide to combinations of either all Group A ceramides (Model Comparison 8) or all Group B ceramides (Model Comparison 9). These model comparisons demonstrate the diagnostic power of selecting ceramides based on the newly identified rule of having at least one Group A ceramide and at least one Group B ceramide.

In Model Comparison 8, combinations of at least one Group A ceramide and at least one Group B ceramide were compared to combinations of only Group A ceramides. In Table 11, 30 model comparisons are shown with their deviance statistics and Chi-square p-value estimates (with p<0.05 denoting significant difference between the models). In all 30 examples with varying model sizes, the p-value for the deviance statistics is less than 0.05 which means that the model with at least one Group A ceramide and at least one Group B ceramide is significantly better in discriminating the case-control grouping as compared to the model with only Group A ceramides.

TABLE 11

Model Comparison 8

| Comparison of combinations from group A + B vs A | Deviance | P-value |
|---|---|---|
| A_Cer(d18:2/24:0) + A_Cer(d18:2/14:0) + B_Cer(d18:1/24:1) + B_Cer(d18:1/24:2) vs A_Cer(d18:2/24:0) + A_Cer(d18:2/14:0) | $-98.1871$ | $4.77*10^{-22}$ |
| A_Cer(d18:2/14:0) + A_Cer(d18:1/25:0) + B_Cer(d18:1/23:1) + B_Cer(d18:1/16:0) vs A_Cer(d18:2/14:0) + A_Cer(d18:1/25:0) | $-96.4759$ | $1.12*10^{-21}$ |
| A_Cer(d18:2/14:0) + A_Cer(d18:1/24:0) + B_Cer(d18:1/16:0) + B_Cer(d18:0/24:1) vs A_Cer(d18:2/14:0) + A_Cer(d18:1/24:0) | $-95.3734$ | $1.95*10^{-21}$ |
| A_Cer(d18:2/24:0) + A_Cer(d18:0/24:0) + B_Cer(d18:1/24:2) vs A_Cer(d18:2/24:0) + A_Cer(d18:0/24:0) | $-87.6104$ | $7.97*10^{-21}$ |
| A_Cer(d18:1/25:0) + B_Cer(d18:1/23:1) + B_Cer(d18:1/24:2) vs A_Cer(d18:1/25:0) | $-91.9287$ | $1.09*10^{-20}$ |
| A_Cer(d16:1/26:0) + A_Cer(d18:1/26:0) + B_Cer(d18:1/24:2) vs A_Cer(d16:1/26:0) + A_Cer(d18:1/26:0) | $-85.5673$ | $2.24*10^{-20}$ |
| A_Cer(d18:1/23:0) + A_Cer(d18:2/23:0) + B_Cer(d18:1/24:2) + B_Cer(d18:1/18:0) vs A_Cer(d18:1/23:0) + A_Cer(d18:2/23:0) | $-87.2167$ | $1.15*10^{-19}$ |
| A_Cer(d18:1/24:0) + B_Cer(d18:1/24:2) + B_Cer(d18:2/16:0) vs A_Cer(d18:1/24:0) | $-86.8036$ | $1.42*10^{-19}$ |
| A_Cer(d18:1/23:0) + B_Cer(d18:1/24:2) vs A_Cer(d18:1/23:0) | $-80.3857$ | $3.08*10^{-19}$ |
| A_Cer(d18:2/25:0) + B_Cer(d18:1/24:2) + B_Cer(d16:1/16:0) vs A_Cer(d18:2/25:0) | $-85.2126$ | $3.14*10^{-19}$ |
| A_Cer(d18:2/14:0) + A_Cer(d18:2/24:0) + B_Cer(d18:0/18:0) + B_Cer(d18:1/16:0) vs A_Cer(d18:2/14:0) + A_Cer(d18:2/24:0) | $-85.2039$ | $3.15*10^{-19}$ |
| A_Cer(d16:1/22:0) + A_Cer(d18:1/25:0) + B_Cer(d18:1/18:0) + B_Cer(d16:1/16:0) vs A_Cer(d16:1/22:0) + A_Cer(d18:1/25:0) | $-84.5342$ | $4.40*10^{-19}$ |
| A_Cer(d18:2/22:0) + A_Cer(d18:1/24:0) + B_Cer(d18:2/16:0) + B_Cer(d18:1/16:0) vs A_Cer(d18:2/22:0) + A_Cer(d18:1/24:0) | $-83.7895$ | $6.39*10^{-19}$ |

TABLE 11-continued

Model Comparison 8

| Comparison of combinations from group A + B vs A | Deviance | P-value |
|---|---|---|
| A_Cer(d16:1/23:0) + A_Cer(d18:2/23:0) + B_Cer(d18:1/24:2) vs A_Cer(d16:1/23:0) + A_Cer(d18:2/23:0) | −78.7667 | $6.99*10^{-19}$ |
| A_Cer(d18:1/23:0) + B_Cer(d18:1/24:2) + B_Cer(d18:0/24:1) vs A_Cer(d18:1/23:0) | −83.1759 | $8.68*10^{-19}$ |
| A_Cer(d18:1/23:0) + B_Cer(d18:1/24:2) + B_Cer(d18:1/24:1) vs A_Cer(d18:1/23:0) | −82.1792 | $1.43*10^{-18}$ |
| A_Cer(d18:1/23:0) + A_Cer(d18:2/22:0) + B_Cer(d18:1/18:0) vs A_Cer(d18:1/23:0) + A_Cer(d18:2/22:0) | −76.7722 | $1.92*10^{-18}$ |
| A_Cer(d18:1/25:0) + B_Cer(d18:1/16:0) + B_Cer(d18:0/16:0) vs A_Cer(d18:1/25:0) | −80.1605 | $3.92*10^{-18}$ |
| A_Cer(d18:1/25:0) + B_Cer(d18:1/23:1) + B_Cer(d18:0/16:0) vs A_Cer(d18:1/25:0) | −77.8771 | $1.23*10^{-17}$ |
| A_Cer(d18:2/14:0) + B_Cer(d18:1/24:2) vs A_Cer(d18:2/14:0) | −72.8176 | $1.42*10^{-17}$ |
| A_Cer(d18:2/22:0) + A_Cer(d18:2/14:0) + B_Cer(d18:0/18:0) + B_Cer(d18:2/24:2) vs A_Cer(d18:2/22:0) + A_Cer(d18:2/14:0) | −77.0652 | $1.84*10^{-17}$ |
| A_Cer(d18:1/25:0) + A_Cer(d18:0/25:0) + B_Cer(d18:1/16:0) + B_Cer(d18:0/24:2) vs A_Cer(d18:1/25:0) + A_Cer(d18:0/25:0) | −77.0528 | $1.85*10^{-17}$ |
| A_Cer(d18:2/24:0) + A_Cer(d18:2/14:0) + B_Cer(d18:1/24:1) + B_Cer(d18:1/23:1) vs A_Cer(d18:2/24:0) + A_Cer(d18:2/14:0) | −76.9415 | $1.96*10^{-17}$ |
| A_Cer(d18:2/22:0) + A_Cer(d16:1/23:0) + B_Cer(d18:1/24:2) + B_Cer(d18:0/24:1) vs A_Cer(d18:2/22:0) + A_Cer(d16:1/23:0) | −76.2966 | $2.71*10^{-17}$ |
| A_Cer(d18:1/24:0) + A_Cer(d18:2/22:0) + B_Cer(d18:1/24:1) vs A_Cer(d18:1/24:0) + A_Cer(d18:2/22:0) | −71.4015 | $2.91*10^{-17}$ |
| A_Cer(d18:2/24:0) + A_Cer(d18:1/24:0) + B_Cer(d16:1/16:0) + B_Cer(d18:1/16:0) vs A_Cer(d18:2/24:0) + A_Cer(d18:1/24:0) | −75.9818 | $3.17*10^{-17}$ |
| A_Cer(d18:1/23:0) + A_Cer(d18:0/24:0) + B_Cer(d18:1/18:0) + B_Cer(d18:2/16:0) vs A_Cer(d18:1/23:0) + A_Cer(d18:0/24:0) | −75.4404 | $4.15*10^{-17}$ |
| A_Cer(d16:1/22:0) + A_Cer(d18:2/26:0) + B_Cer(d16:1/16:0) + B_Cer(d18:1/18:0) vs A_Cer(d16:1/22:0) + A_Cer(d18:2/26:0) | −75.3128 | $4.43*10^{-17}$ |
| A_Cer(d18:1/26:0) + B_Cer(d18:1/18:0) + B_Cer(d18:2/18:0) vs A_Cer(d18:1/26:0) | −74.8376 | $5.61*10^{-17}$ |
| A_Cer(d18:1/25:0) + A_Cer(d18:0/24:0) + B_Cer(d18:0/24:1) + B_Cer(d18:1/23:1) vs A_Cer(d18:1/25:0) + A_Cer(d18:0/24:0) | −73.7486 | $9.68*10^{-17}$ |

In Model Comparison 9, combinations of at least one Group A ceramide and at least one Group B ceramide were compared to combinations of only Group B ceramides. In Table 12, 30 model comparisons are shown with their deviance statistics and Chi-square p-value estimates (with p<0.05 denoting significant difference between the models).

In all 30 examples with varying model sizes, the p-value for the deviance statistics is less than 0.05 which means that the model with at least one Group A ceramide and at least one Group B ceramide is significantly better in discriminating the case-control grouping as compared to the model with only Group B ceramides.

TABLE 12

Model Comparison 9

| Comparison of combinations from groups A + B vs B | Deviance | P-value |
|---|---|---|
| A_Cer(d18:2/26:0) + A_Cer(d16:1/22:0) + B_Cer(d16:1/16:0) + B_Cer(d18:2/24:2) vs B_Cer(d16:1/16:0) + B_Cer(d18:2/24:2) | −87.9369 | $8.03*10^{-20}$ |
| A_Cer(d18:2/24:0) + A_Cer(d18:2/26:0) + B_Cer(d18:1/24:2) vs B_Cer(d18:1/24:2) | −87.3635 | $1.07*10^{-19}$ |
| A_Cer(d18:2/24:0) + A_Cer(d18:1/26:0) + B_Cer(d18:1/24:2) vs B_Cer(d18:1/24:2) | −87.3635 | $1.07*10^{-19}$ |
| A_Cer(d18:2/24:0) + A_Cer(d18:1/26:0) + B_Cer(d18:1/16:0) + B_Cer(d18:2/24:2) vs B_Cer(d18:1/16:0) + B_Cer(d18:2/24:2) | −84.6387 | $4.18*10^{-19}$ |
| A_Cer(d18:2/25:0) + B_Cer(d18:2/24:2) vs B_Cer(d18:2/24:2) | −69.1183 | $9.27*10^{-17}$ |
| A_Cer(d16:1/22:0) + A_Cer(d18:2/25:0) + B_Cer(d18:2/16:0) + B_Cer(d18:2/24:2) vs B_Cer(d18:2/16:0) + B_Cer(d18:2/24:2) | −73.37 | $1.17*10^{-16}$ |
| A_Cer(d18:2/24:0) + B_Cer(d18:2/24:2) vs B_Cer(d18:2/24:2) | −66.7609 | $3.07*10^{-16}$ |
| A_Cer(d18:2/25:0) + A_Cer(d16:1/23:0) + B_Cer(d18:0/24:2) + B_Cer(d18:2/24:2) vs B_Cer(d18:0/24:2) + B_Cer(d18:2/24:2) | −70.7431 | $4.35*10^{-16}$ |
| A_Cer(d18:2/24:0) + B_Cer(d18:1/24:2) vs B_Cer(d18:1/24:2) | −65.5054 | $5.80*10^{-16}$ |
| A_Cer(d18:1/23:0) + A_Cer(d18:2/26:0) + B_Cer(d18:1/16:0) + B_Cer(d18:1/24:2) vs B_Cer(d18:1/16:0) + B_Cer(d18:1/24:2) | −70.074 | $6.08*10^{-16}$ |
| A_Cer(d18:2/14:0) + A_Cer(d18:2/26:0) + B_Cer(d18:0/24:1) + B_Cer(d18:1/24:2) vs B_Cer(d18:0/24:1) + B_Cer(d18:1/24:2) | −68.4406 | $1.38*10^{-15}$ |
| A_Cer(d16:1/24:0) + A_Cer(d18:1/23:0) + B_Cer(d16:1/16:0) vs B_Cer(d16:1/16:0) | −68.0755 | $1.65*10^{-15}$ |
| A_Cer(d18:2/24:0) + A_Cer(d18:2/25:0) + B_Cer(d18:1/23:1) + B_Cer(d18:1/24:1) vs B_Cer(d18:1/23:1) + B_Cer(d18:1/24:1) | −67.43 | $2.28*10^{-15}$ |
| A_Cer(d18:1/26:0) + B_Cer(d18:1/23:1) + B_Cer(d18:1/16:0) vs B_Cer(d18:1/23:1) + B_Cer(d18:1/16:0) | −61.4525 | $4.54*10^{-15}$ |
| A_Cer(d18:2/24:0) + A_Cer(d18:2/23:0) + B_Cer(d18:1/24:2) vs B_Cer(d18:1/24:2) | −65.9445 | $4.79*10^{-15}$ |
| A_Cer(d18:2/25:0) + A_Cer(d18:0/24:0) + B_Cer(d18:1/24:1) vs B_Cer(d18:1/24:1) | −65.7703 | $5.23*10^{-15}$ |
| A_Cer(d18:0/24:0) + A_Cer(d18:1/25:0) + B_Cer(d18:1/24:2) + B_Cer(d18:2/22:1) vs B_Cer(d18:1/24:2) + B_Cer(d18:2/22:1) | −64.4492 | $1.01*10^{-14}$ |
| A_Cer(d18:1/26:0) + B_Cer(d18:1/24:2) vs B_Cer(d18:1/24:2) | −59.7105 | $1.10*10^{-14}$ |
| A_Cer(d18:0/25:0) + A_Cer(d18:1/25:0) + B_Cer(d18:1/23:1) + B_Cer(d18:0/16:0) vs B_Cer(d18:1/23:1) + B_Cer(d18:0/16:0) | −63.3033 | $1.79*10^{-14}$ |

TABLE 12-continued

Model Comparison 9

| Comparison of combinations from groups A + B vs B | Deviance | P-value |
|---|---|---|
| A_Cer(d18:1/25:0) + A_Cer(d18:2/25:0) + B_Cer(d18:1/24:2) + B_Cer(d18:2/24:2) vs B_Cer(d18:1/24:2) + B_Cer(d18:2/24:2) | −62.2116 | $3.10*10^{-14}$ |
| A_Cer(d18:2/14:0) + A_Cer(d18:2/25:0) + B_Cer(d18:1/16:0) + B_Cer(d18:2/18:0) vs B_Cer(d18:1/16:0) + B_Cer(d18:2/18:0) | −61.1778 | $5.19*10^{-14}$ |
| A_Cer(d18:1/26:0) + B_Cer(d18:1/23:1 ) + B_Cer(d18:1/24:1) vs B_Cer(d18:1/23:1) + B_Cer(d18:1/24:1) | −56.5949 | $5.35*10^{-14}$ |
| A_Cer(d18:1/25:0) + B_Cer(d18:0/24:2) + B_Cer(d18:1/24:1) vs B_Cer(d18:0/24:2) + B_Cer(d18:1/24:1) | −55.574 | $9.00*10^{-14}$ |
| A_Cer(d18:2/24:0) + B_Cer(d18:2/24:2) + B_Cer(d18:1/23:1) vs B_Cer(d18:2/24:2) + B_Cer(d18:1/23:1) | −55.4461 | $9.61*10^{-14}$ |
| A_Cer(d18:2/24:0) + A_Cer(d18:0/24:0) + B_Cer(d18:2/18:0) vs B_Cer(d18:2/18:0) | −59.9392 | $9.65*10^{-14}$ |
| A_Cer(d18:0/24:0) + A_Cer(d18:1/25:0) + B_Cer(d18:0/16:0) vs B_Cer(d18:0/16:0) | −59.55 | $1.17*10^{-13}$ |
| A_Cer(d18:1/23:0) + A_Cer(d18:2/24:0) + B_Cer(d18:2/16:0) vs B_Cer(d18:2/16:0) | −58.8706 | $1.65*10^{-13}$ |
| A_Cer(d18:2/25:0) + B_Cer(d18:2/16:0) + B_Cer(d18:0/24:2) vs B_Cer(d18:2/16:0) + B_Cer(d18:0/24:2) | −54.189 | $1.82*10^{-13}$ |
| A_Cer(d18:2/26:0) + A_Cer(d18:2/22:0) + B_Cer(d18:1/24:1) vs B_Cer(d18:1/24:1) | −58.6415 | $1.85*10^{-13}$ |
| A_Cer(d18:2/24:0) + A_Cer(d18:0/25:0) + B_Cer(d16:1/16:0) + B_Cer(d18:0/18:0) vs B_Cer(d16:1/16:0) + B_Cer(d18:0/18:0) | −57.6935 | $2.96*10^{-13}$ |

Thus, the results of this study demonstrate at least the following trends: (1) combining at least one Group A ceramide and at least one Group B ceramide significantly improves their discriminatory power as compared to a Group A ceramide or Group B ceramide alone; (2) increasing the number of Group A and Group B ceramides significantly increases the discriminatory power if the combination of ceramides includes at least one Group A and at least one Group B ceramide; (3) increasing the number of Group A ceramides (without a Group B ceramide) does not significantly improve the discriminatory power of the combined ceramides; (4) increasing the number of Group B ceramides (without a Group A ceramide) does not significantly improve the discriminatory power of the combined ceramides; and (5) increasing the number of ceramides that do not fall within either Group A or Group B does not significantly improve the discriminatory power of the combined ceramides.

Accordingly, these data have helped to establish a new rule for selecting ceramide biomarkers to predict CV complications with significantly improved discriminatory power (discriminating patients at risk to develop CV complications from control patients). By following the new selection rule and combining at least one Group A ceramide with at least one Group B ceramide, the case control grouping can be significantly more accurate as compared to individual markers or lipid ratios or combinations of ceramide markers that are not selected according to this selection rule.

While this invention has been particularly shown and described with references to preferred embodiments thereof, it will be understood by those skilled in the art that various changes in form and details may be made therein without departing from the scope of the invention encompassed by the appended claims

The invention claimed is:

1. A method for evaluating the effectiveness of a treatment of CVD and/or one or more of its complications in a human subject, wherein the method comprises:
   (a) determining in a biological sample obtained from the human subject the concentration of at least one ceramide of Formula (I):

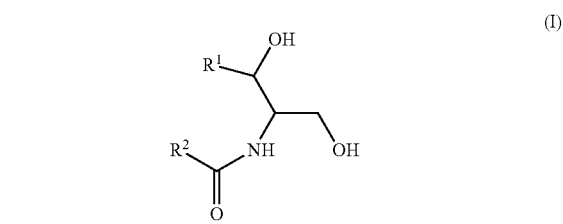

(I)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 21-25 carbon atoms, and wherein the biological sample is a blood sample, blood serum sample, a blood plasma sample, or a lipoprotein fraction obtained therefrom;

(b) determining in the biological sample from the human subject the concentration of at least one ceramide of Formula (II):

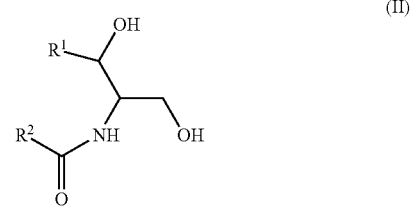

(II)

wherein $R^1$ is a mono-unsaturated alkyl chain having 13 carbon atoms or a saturated, mono-unsaturated or di-unsaturated alkyl chain having 15 carbon atoms, and wherein $R^2$ is a saturated alkyl chain having 15 or 17 carbon atoms, a mono-unsaturated alkyl chain having 21-23 carbon atoms, or a di-unsaturated alkyl chain having 23 or 25 carbon atoms;

(c) comparing the concentration of the at least one ceramide of Formula (I) and the concentration of the at least one ceramide of Formula (II) to a control sample, and (d) determining that the treatment is effective if the sample contains an increased concentration of the at least one ceramide of Formula (I) and a decreased concentration of the at least one ceramide of Formula (II), as compared to the control sample, wherein the method further comprises spiking the biological sample with at least one isotope-labelled ceramide of Formula (I) and at least one isotope-labelled ceramide of Formula (II) prior to determining the concentration of the at least one ceramide of Formula (I) and the at least one ceramide of Formula (II) and wherein the one or more CVD complications comprise one or more of acute myocardial infarction (AMI), acute coronary syndrome (ACS), stroke and cardiovascular death.

2. The method of claim 1, wherein the concentrations of the at least one ceramide of Formula (I) and the at least one ceramide of Formula (II) are determined using a mass spectrometry instrument, and optionally wherein the mass spectrometry instrument coupled to a direct sample infusion method or to a high-performance separation method.

3. The method of claim 1, wherein concentrations of at least 2, at least 3, at least 4, at least 5 or at least 6 ceramides of Formula (I) and/or at least 2, at least 3, at least 4, at least 5 or at least 6 ceramides of Formula (II) are determined.

4. The method of claim 1, wherein the concentrations of the following ceramides of Formula (II) are determined: Cer(d18:1/16:0), Cer(d18:1/18:0) and/or Cer(d18:1/24:1) and/or wherein the concentration of the following ceramide of Formula (I) is determined: Cer(d18:1/24:0).

5. The method of claim 1, further comprising a step of extracting lipids from the biological sample prior to determining the concentration of the at least one ceramide of Formula (I) and the at least one ceramide of Formula (II).

6. The method of claim 1, wherein the isotope is deuterium.

7. The method of claim 1, further comprising determining the blood, serum or plasma level of total cholesterol, low-density lipoprotein cholesterol (LDL-C), high-density lipoprotein cholesterol (HDL-C), Apolipoprotein A-I (ApoAI), Apolipoprotein A-II (ApoAII), Apolipoprotein B (ApoB) and/or Apolipoprotein C-III (ApoC-III) in a sample from said subject.

8. The method of claim 1, further comprising, after the determining step, changing, supplementing, or keeping the same, an already administered treatment in the human subject from whom the biological sample was obtained based on the concentrations of the at least one ceramide of Formula (I) and the at least one ceramide of Formula (II).

9. The method of claim 1, wherein the human subject is undergoing a lipid-lowering drug treatment and optionally wherein the lipid-lowering drug treatment is a statin treatment.

10. The method of claim 1, wherein the method further comprises:
(e) administering a treatment to the subject if the determining steps indicate the treatment is not effective.

11. The method of claim 1, further comprising individual tailoring of treatment, life counseling, drug intervention and/or follow-up for the human subject from whom the biological sample was obtained if the determining steps indicate the treatment is not effective.

* * * * *